(12) United States Patent
Liotta et al.

(10) Patent No.: US 9,005,996 B2
(45) Date of Patent: Apr. 14, 2015

(54) METHOD OF ISOLATING ANALYTES FROM A SAMPLE

(75) Inventors: Lance Liotta, Bethesda, MD (US); Emanuel Petricoin, Gainesville, VA (US); David Geho, Blue Bell, PA (US)

(73) Assignee: George Mason Research Foundation, Fairfax, VA (US)

( * ) Notice: Subject to any disclaimer, the term of this patent is extended or adjusted under 35 U.S.C. 154(b) by 1625 days.

(21) Appl. No.: 11/527,727

(22) Filed: Sep. 27, 2006

(65) Prior Publication Data

US 2010/0240543 A1  Sep. 23, 2010

Related U.S. Application Data

(60) Provisional application No. 60/720,466, filed on Sep. 27, 2005, provisional application No. 60/759,574, filed on Jan. 18, 2006.

(51) Int. Cl.
*G01N 33/545* (2006.01)
*G01N 33/543* (2006.01)

(52) U.S. Cl.
CPC ................. *G01N 33/54346* (2013.01)

(58) Field of Classification Search
None
See application file for complete search history.

(56) References Cited

U.S. PATENT DOCUMENTS

| 4,138,474 A | 2/1979 | Updike |
| 2002/0182658 A1 | 12/2002 | Polak et al. |
| 2003/0232340 A1 | 12/2003 | Anderson |

OTHER PUBLICATIONS

Geho et al., "Opportunities for Nanotechnology—Based Innovation in Tissue Proteomics," Biomedical Microdevices, vol. 6, No. 1, 2004, pp. 231-239.
Geho et al., "Nanoparticles: potential biomarker harvesters," Current Opinion in Chemical Biology, vol. 10, 2006, pp. 56-61.
Nayak et al., "Ligand—Functionalized Core/Shell Microgels with Permselective Shells," Angew. Chem., vol. 116, 2004, pp. 6874-6877.
Sassi et al., "Partitioning of Proteins and Small Biomolecules in Temperature- and pH-Sensitive Hydrogels," Polymer, vol. 37, No. 11, 1996, pp. 2151-2164.
Terracciano et al., "Selective Binding and Enrichment for Low-Molecular Weight Biomarker Molecules in Human Plasma After Exposure to Nanoporous Silica Particles," Proteomics, vol. 6, 2006, pp. 3243-3250.
Boschetti, "Advanced Sorbents for Preparative Protein Separation Purposes," Journal of Chromatograpy, vol. 658, No. 2, 1994, pp. 207-236.
Nahar et al., "Functional Polymeric Nanoparticles: An Efficient and Promising Tool for Active Delivery of Bioactives," Critical Reviews in Therapeutic Drug Carrier Systems, vol. 23, No. 4, 2006, pp. 259-318.

(Continued)

*Primary Examiner* — Chris L Chin
(74) *Attorney, Agent, or Firm* — Michael L. Greenberg, Esq.; Greenberg & Lieberman, LLC

(57) ABSTRACT

The current invention is a capture-particle comprising: a) a molecular sieve portion; and b) an analyte binding portion; wherein the molecular sieve portion, analyte binding portion or both further comprise a cross-linked region having modified porosity. Capture particles wherein the molecular sieve portion, analyte binding portion or both comprise pore dimensions sufficient to exclude molecules larger than about 60 kDa. These particles are useful in purification and diagnostic methods. Kits comprising the capture particles are also described.

16 Claims, 16 Drawing Sheets

(56) References Cited

OTHER PUBLICATIONS

Camerini et al., "A Method for the Selective Isolation and Enrichment of Carrier Protein-Bound Low-Molecular Weight Proteins and Peptides in the Blood," Proteomics Clin. Appl., vol. 1, 2007, pp. 176-184.

Basinska, "Hydrophilic Core-Shell Microspheres: A suitable Support for Controlled Attachment of Proteins and Biomedical Diagnostics," Macromolecular Bioscience, vol. 5, 2005, pp. 1145-1168.

Woo et al., "Preparation and Characterization of a Composite PLGA and Poly (Acryloyl Hydroxyethyl Starch) Mocrosphere System for Protein Delivery," Pharmaceutical Research, vol. 18, No. 11, Nov. 2001, pp. 1600-1606.

Sparnacci et al., "Core-Shell Michrospheres by Dispersion Polymerization as Promising Delivery Systems for Proteins," J. Biomater. Sci. Polymer Edn., vol. 16, No. 12, 2006, pp. 1557-1574.

Pelton, "Temperature-Sensitive Aqueous Microgels," Advances in Colloid and Interface Science, vol. 85, 2000, pp. 1-33.

Saunders et al., "Microgel Particles as Model Colloids: Theory, Properties and Applications," Advances in Colloid and Interface Science, vol. 80, 1999, pp. 1-25.

Adkins et al., "Toward a Human Blood Serum Proteome," Molecular & Cellular Proteomics, vol. 1, 2002, pp. 947-955.

Aebersold et al., "Perspective: A program to Improve Protein Biomarker Discovery for Cancer," Journal of Proteome Research, vol. 4, 2005, pp. 1104-1109.

Anderson et al., "The Human Plasma Proteome: History, Character and Diagnostic Prospects," Molecular & Cellular Proteomics, vol. 1, 2002, pp. 845-867.

Ayache et al., "Effects of Storage Time and Exogenous Protease Inhibitors on Plasma Protein Levels," American Journal of Clinical Pathology, vol. 126, 2006, pp. 174-184.

Conrads et al., "Sampling and Analytical Strategies for Biomarker Discovery Using Mass Spectrometry," BioTechniques, vol. 40, Jun. 2006, pp. 799-805.

Downie et al., "Assessment of the Stability of N-Terminal Pro-Brain Natriuretic Peptide In Vitro: Implications for Assessment of Left Ventricular Dysfunction," Clinical Science, vol. 97, 1999, pp. 255-258.

Elias et al., "Comparative Evaluation of Mass Spectrometry Platforms Used in Large-Scale Proteomics Investigations," Nature Methods, vol. 2, No. 9, Sep. 2005, pp. 667-675.

Ellis et al., "Metabolic Fingerprinting as a Diagnostic Tool," Pharmacogenomics, vol. 8, No. 9, 2007, pp. 1243-1266.

Espina et al., "Protein Microarrays: Molecular Profiling Technologies for Clinical Specimens," Proteomics, vol. 3, 2003, pp. 2091-2100.

Etzioni et al., "The Case for Early Detection," Nature Reviews, vol. 3, Apr. 2003, pp. 1-10.

Gan et al., "Fluorescence Nonradiative Energy Transfer Analysis of Crosslinker Heterogeneity in Core-Shell Hydrogel Nanoparticles," Analytica Chimica Acta, vol. 496, 2003, pp. 53-63.

Gan et al., "Synthesis and Protein Adsorption Resistance of PEG-Modified Poly(N-isopropylacrylamide) Core/Shell Microgels," Macromolecules, vol. 35, 2002, pp. 9634-9639.

Geho et al., "Fractionation of Serum Components Using Nanoporous Substrates," Bioconjugate Chem., vol. 17, 2006, pp. 654-661.

Griffin et al., "Tumor Metabolomics in Animal Models of Human Cancer," Journal of Proteome Research, vol. 6, 2007, pp. 498-505.

Gulmann et al., "Array-Based Proteomics: Mapping of Protein Circuitries for Diagnostics, Prognostics, and Therapy Guidance in Cancer," Journal of Pathology, vol. 208, 2006, pp. 595-606.

Haupt et al., "Molecularly Imprinted Polymers and Their Use in Biomimetic Sensors," Chem. Rev., vol. 100, 2000, pp. 2495-2504.

Hiratani et al., "Controlling Drug Release from Imprinted Hydrogels by Modifying the Characteristics of the Imprinted Cavities," Macromolecular Bioscience, vol. 5, 2005, pp. 728-733.

Ito et al., "Preparation of Thermosensitive Submicrometer Gel Particles with Anionic and Cationic Charges," Langmuir, vol. 15, 1999, pp. 4289-4294.

Ivanov et al., "Interaction of Sugars, Polysaccharides and Cells with Boronate-Containing Copolymers: from Solution to Polymer Brushes," Journal of Molecular Recognition, vol. 19, 2006, pp. 322-331.

Jones et al., "Synthesis and Characterization of Multiresponsive Core-Shell Microgels," Macromolecules, vol. 33, 2000, pp. 8301-8306.

Liu et al., "Preparation and Characterization of Smart Magnetic Hydrogels and its use for Drug Release," Journal of Magentism and Magnetic Materials, vol. 304, 2006, pp. e397-e399.

Lopez et al., "A Novel, High-Troughput Workflow for Discovery and Identification of Serum Carrier Protein-Bound Peptide Biomarker Candidates in Ovarian Cancer Samples," Clinical Chemistry, vol. 23, No. 6, 2007, pp. 1067-1074.

Lopez et al., "High-Resolution Serum Proteomic Profiling of Alzheimer Desease Samples Reveals Disease-Specific, Carrier-Protein—Bound Mass Signatures," Clinical Chemistry, vol. 53, No. 10, 2005, pp. 1946-1954.

Lowenthal et al., "Analysis of Albumin—Associated Peptides and Proteins from Ovarian Cancer Patients," Clinical Chemistry, vol. 51, No. 10, 2005, pp. 1933-1945.

Merrell et al., "Analysis of Low-Abundance, Low-Molecular-Weight Serum Proteins Using Mass Spectrometry," Journal of Biomolecular Techniques, vol. 15, Issue 4, Dec. 2004, pp. 238-248.

Nayak et al., "Soft Nanotechnology with Soft Nanoparticles," Angewandte Chemie Int. Ed., vol. 44, 2005, pp. 7686-7708.

Nolan et al., "Phase Transititon Behavior, Protein Adsorption, and Cell Adhesion Resistance of Poly(ethylene glycol) Cross-Linked Mocrogel Particles," Biomacromolecules, vol. 6, 2005, pp. 2032-2039.

Orvisky et al., "Enrichment of Low Molecular Weight Fraction of Serum for MS Analysis of Peptides Associated with Hepatocellular Carcinoma," Proteomics, vol. 6, 2006, pp. 2895-2902.

Park et al., "Adsorption and Thermoresponsive Behavior of Poly(N-isopropylacrylamide-co-N,N'-cystaminebisacrylamide) Thin Film on Gold," Langmuir, vol. 23, 2007, pp. 7083-7089.

Rifai et al., "Protein Biomarker Discovery and Validation: the Long and Uncertain Path to Clinical Utility," Nature Biotechnology, vol. 24, No. 8, Aug. 2006, pp. 971-983.

Rozen et al., "Metabolomic Analysis and Signatures in Motor Neuron Disease," Metabolomics, vol. 1, No. 2, Apr. 2005, pp. 101-108.

Srinivas et al., "Proteomics for Cancer Biomarker Discovery," Clinical Chemistry, vol. 48, No. 8, 2002, pp. 1160-1169.

Tanaka et al., "Phase Transitions in Ionic Gels," Physical Review Letters, vol. 45, No. 20, Nov. 17, 1980, pp. 1636-1639.

Tanaka et al., "Critical Kinetics of Volume Phase Transition of Gels," Physical Review Letters, vol. 55, No. 22, Nov. 25, 1985, pp. 2455-2458.

Tanaka, "Collapse of Gels and the Critical Endpoint," Physical Review Letters, vol. 40, No. 12, Mar. 20, 1978, pp. 820-823.

Jones et al., "Shell-Restricted Swelling and Core Compression in Poly(N-isopropylacrylamide) Core-Shell Microgels," Macromolecules, vol. 36, 2003, pp. 1988-1993.

Tanaka, et al., "Phase Separation and Gelation in Gelatin Gels," Physical Review Letters, vol. 42, No. 23, Jun. 4, 1979, pp. 1556-1559.

Ulmert et al., "Reproducibility and Accuracy of Measurements of Free and Total Prostate-Specific Antigen in Serum vs. Plasma After Long-Term Storage at -20° C.," Clinical Chemistry, vol. 52, No. 2, 2006, pp. 235-239.

Villanueva et al., "Differential Exoprotease Activities Confer Tumor-Specific Serum Peptidome Patterns," The Journal of clinical Investigation, vol. 116, No. 1, Jan. 2006, pp. 271-284.

Wu et al., "Evaluating Proteins Release From, and Their Interactions With, Thermosensitive Poly (N-isopropylacrylamide) Hydrogels," Journal of Controlled Release, vol. 102, 2005, pp. 361-372.

Yates et al., "Method to Correlated Tandem Mass Spectra of Modified Peptides to Amino Acid Sequences in the Protein Database," Analytical Chemistry, vol. 67, No. 8, Apr. 15, 1995, pp. 1426-1436.

Zhang et al., "Fabrication and Characterization of a Smart Drug Delivery System: Microsphere in Hydrogel," Biomaterials, vol. 26, 2005, pp. 3299-3309.

(56) References Cited

OTHER PUBLICATIONS

Zolotarjova et al., "Differences Among Techniques for High-Abundant Protein Depletion," Proteomics, vol. 5, 2005, pp. 3304-3313.
Frank et al., "Clinical Biomarkers in Drug Discovery and Development;" Nature Reviews Drug Discovery, vol. 2, Jul. 2003, pp. 566-580.
Tirumalai et al., "Characterization of the Low Molecular Weight Human Serum Proteome," Molecular and Cellular Proteomics, vol. 2, No. 10, 2003, pp. 1096-1103.
Keshishian et al., "Quantitative, Multiplexed Assays for Low Abundance Proteins in Plasma by Targeted Mass Spectometry and Stable Isotope Dilution," Molecular and Cellular Proteomics, vol. 6, No. 12, 2007, pp. 2212-2229.
Fernandez-Nieves et al., "Charge Controlled Swelling of Microgel Particles," Macro Molecules, vol. 33, 2000, pp. 2114-2118.
Ray M. Bowen, "Theory of Mixtures," Academic Press, Inc., New York, 1976.
Robert Pelton, "Temperature-Sensitive Aqueous Microgels," Advances in Colloid and Interface Science, vol. 85, 2000, pp. 1-33.
Sparnacci et al., "Core-Shell Microspheres by Dispersion Polymerization as Promising Delivery Systems for Proteins," Journal of Biomaterials Science, Polymer Edition, vol. 16, No. 12, 2005, pp. 1557-1574.

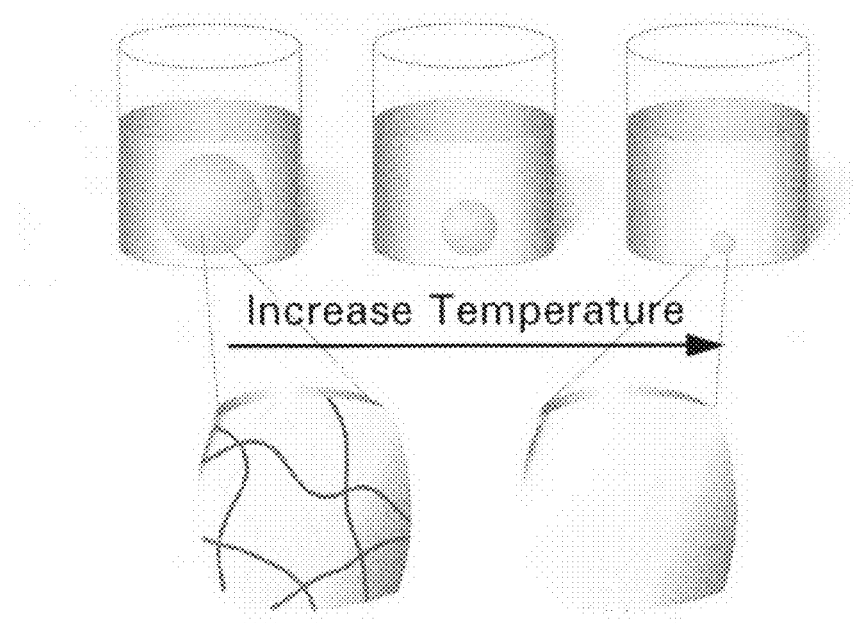
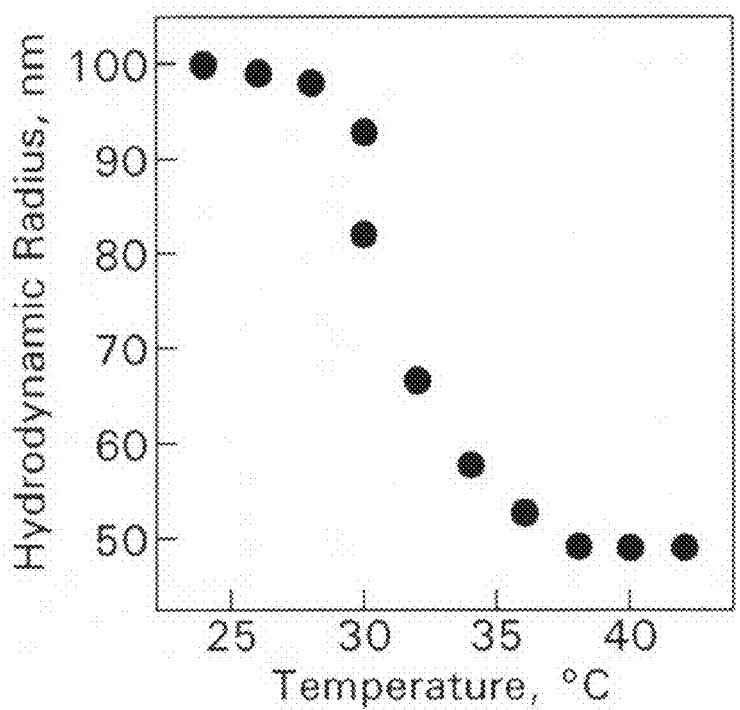
FIG. 2

Released Polypeptides

- Keratin
- Ig gamma-1 chain
- Calgranulin A
- Vitamin D binding protein
- S100 calcium binding protein
- Filaggrin
- Serum Albumin precursor
- Thioredoxin
- Desmoplakin
- GFAP
- Annexin A2
- Galectin-7
- Dermicidin precursor
- Collagenase 3 precursor
- Haptoglobin precursor
- Nuclear RNA export factor 1
- Zinc finger protein 226
- Cell division cycle associated 1
- Annexin A6
- Nuclear pore complex protein Nup 155
- Ubiquitin carboxy-terminal hydrolase 47
- Involucrin
- SCCA-1

| Protein | pI | MW |
|---|---|---|
| Parvalbumin | 4.1 | 12K |
| Ovalbumin | 4.6 | 45K |
| Albumin | 4.9 | 60K |
| B Lactoglobulin | 5.2 | 23K |
| Actin | 5.2 | 43K |
| Insulin | 5.4 | 6K |
| Myoglobin | 7.0 | 17K |
| Ribonuclease A | 7.8 | 14K |
| Cytochrome C | 10.6 | 12K |
| Lysozyme | 11.0 | 14K |

| Protein | pI | MW |
|---|---|---|
| Insulin | 5.4 | 6K |
| Parvalbumin | 4.1 | 12K |
| Cytochrome C | 10.6 | 12K |
| Ribonuclease A | 7.8 | 14K |
| Lysozyme | 11.0 | 14K |
| Myoglobin | 7.0 | 17K |
| B Lactoglobulin | 5.2 | 23K |
| Actin | 5.2 | 43K |
| Ovalbumin | 4.6 | 45K |
| Albumin | 4.6 | 60K |

FIG. 12

US 9,005,996 B2

METHOD OF ISOLATING ANALYTES FROM A SAMPLE

CROSS-REFERENCE TO RELATED PATENT APPLICATIONS

This application claims priority from Provisional U.S. Applications 60/720,466, filed Sep. 27, 2005, and 60/759,574, filed Jan. 18, 2006, incorporated herein by reference in their entirety.

BACKGROUND

There has recently been a surge of interest in the value and clinical potential of proteomic biomarkers (1). A general belief in the medical community is that the earlier a disease is treated, the more successful the therapeutic outcome (2). Consequently, the routine clinical availability of biomarker tests specific for early-stage neoplastic diseases has tremendous potential to dramatically improve public health, even using currently utilized therapeutic modalities. For example, clinical oncologists expect that biomarker detection of pre-metastatic solid tumors of the breast, lung, ovary, and colon could lead to a significant improvement in survival (2). Unfortunately, despite the urgent clinical need, in the past ten years, for all disease categories combined, only a handful of novel biomarkers have graduated to routine clinical use (3). The slow biomarker pipeline persists despite considerable efforts within diagnostics research. The reasons for this failure stem from fundamental technical and biologic roadblocks spanning the biomarker development pipeline from biomarker identification and measurement to initial clinical validation. Two of these major roadblocks are:

Low Abundance: Disease-relevant biomarkers may exist in exceedingly low concentrations within a complex mixture of body fluid proteins containing high-abundance proteins such as albumin.

Instability: Immediately after the blood or other body fluid is collected (e.g. by venipuncture), degradation of proteins can occur, which is mediated by endogenous or exogenous proteinases.

Sensitive and specific biomarkers are expected to exist in very low abundance. There is a great need to develop novel methods for enriching the yield of rare candidate biomarkers present in the small volumes of blood available in clinical study sets. Candidate biomarkers are expected to exist in very low concentrations and must be separated from high-abundance blood proteins, such as albumin, which exist in a billion-fold excess. Early-stage disease lesions such as premalignant cancer may arise within a tissue volume of less than 0.10 mL. Assuming all the putative biomarkers emanating from this volume are uniformly dispersed within the entire blood volume of 5,000 mL, then the dilution factor will be 50,000. One can also reasonably hypothesize that the most physiologically relevant proteins specific for the disease may constitute a minor subpopulation of the cellular proteome. Consequently, the greatest challenge to biomarker discovery is the isolation of very rare candidate proteins within a highly concentrated complex mixture of blood proteins massively dominated by non-relevant proteins. Thus, analytical sensitivity is the first challenge for biomarker discovery and measurement. The problem of low abundance protein detection extends from discovery to routine measurement. During the discovery phase, it is likely that large plasma or serum volumes, including pooled samples, can be available for analysis. In contrast, once a candidate marker is taken forward to clinical testing, the volume of blood available for an individual patient's assay may be less than 1.0 mL. Taking all of these factors into consideration, the analytical platform used to measure the candidate marker must have a detection sensitivity sufficient to reliably detect marker concentrations in the sub-femtomolar or attomolar concentration.

In addition, candidate blood biomarkers are highly perishable. Circulating protein biomarkers are subject to rapid proteolytic cleavage and modification immediately following blood procurement. The level of degradation depends on the manner of collection and the storage conditions immediately following venipuncture. For collection of serum, proteins are subject to cleavage by active enzymes in the clotting cascade. Depending on the time and temperature of incubation during clotting and the temperature of subsequent storage of the separated serum, the constellation of proteolytic fragments can be quite variable (4). If plasma is collected, clotting enzyme activity is suppressed, but endogenous proteinases may still be active. Moreover, depending on the means of plasma stabilization (e.g., heparin versus citrate), there can be significant chemical modifications of plasma proteins. Questionable stability of plasma or serum proteomics markers has been a major cause of perceived bias during the clinical validation of candidate protein biomarkers (5).

SUMMARY OF THE INVENTION

In one embodiment, the current invention describes a capture-particle comprising: a) a molecular sieve portion; and b) an analyte binding portion; wherein the molecular sieve portion, analyte binding portion or both further comprise a cross-linked region having modified porosity.

In other embodiments of the current invention, the analyte binding portion may comprise at least one type of moiety capable of chemically or electrostatically binding and/or sequestering an analyte. Additionally, the analyte binding portion may comprise a carboxy group, amine group, lipid, phosphoprotein, phospholipids, amide group, hydroxyl group, ester group, acrylic group, thiol group, acrylic acid, antibodies, binding proteins, binding pairs, metals, chelating agents, nucleic acids, aptamers, enzyme-binding pockets, lectins, pharmacologic agent, synthetic peptides, antibody fragments, hydrophobic surface, hydrophyllic surface, any derivatives thereof or a combination thereof. The capture-particle may further comprise an analyte bound to the analyte binding portion, said analyte comprising: organic molecules, inorganic molecules, polypeptides, carbohydrates, nucleic acids, lipids, derivatives thereof or any combination thereof.

In other embodiments, the molecular sieve portion is an outer shell enclosing an inner core, said inner core comprising the analyte binding portion. In additional embodiments, the average particle size radius of less than about 100 µm. The molecular sieve portion, analyte binding portion or both may comprise: polyacrylamide, poly(N-isopropylacrylamide), N-alkyl substituted polyacrylamide, poly(N-vinylalkylamide), poly(methacrylic acid), poly(benzyl glutamate), ply (2-ethylacrylic acid), poly(4-vinylpyridine), derivatives thereof or any combination thereof.

In other embodiments, the cross-linked region comprises N,N'-methylenebisacrylamide, ethylene glycol dimethacrylate, tetraethylene glycol dimethacrylate, poly(ethyleneglycol)dimethacrylate or any combination thereof. In other embodiments, the molecular sieve portion, analyte binder portion or both comprise a hydrogel. In some embodiments, the molecular sieve portion, analyte binding portion or both have an average pore size of between about 2 to about 20 nm.

In other embodiments, the molecular sieve portion, analyte binding portion or both have an average pore size of less than about 100 nm.

In other embodiments, the capture-particle releases a bonded or sequestered analyte, changes volume or both when exposed to a physical or chemical treatment. The physical or chemical treatment comprises exposure to: electrical charge, hydrostatic pressure, change in pH, change in temperature, acidic agent, basic agent, UV, ultrasound, x-ray, or a combination thereof.

In other embodiments, the capture particle has the ability to uptake a 1404 Da peptide with substantially no uptake of albumin, has the ability to uptake insulin, or both.

In other embodiments, the current invention describes a capture-particle comprising: a) a molecular sieve portion; and b) an analyte binding portion; wherein the molecular sieve portion, analyte binding portion or both comprise pore dimensions sufficient to exclude molecules larger than about 60 kDa. In further embodiments, the molecular sieve portion, analyte binding portion or both comprise clatherin, viral protein, polypeptides, nucleic acids, carbohydrates, polymeric carbon, or a combination thereof. In other embodiments, the molecular sieve portion, analyte binding portion or both comprise: ferroelectric liquid crystalline elastomers, piezoelectric polymers, "smart" gels, ceramics alloys, silica, carbon nanotubes, or any combination thereof.

In other embodiments, the analyte binding portion comprises at least one type of moiety capable of chemically or electrostatically binding or sequestering an analyte. In other embodiments, the analyte binding portion comprises a carboxy group, amine group, lipid, phosphoprotein, phospholipids, amide group, hydroxyl group, ester group, acrylic group, thiol group, acrylic acid, antibodies, binding proteins, binding pairs, metals, chelating agents, nucleic acids, aptamers, enzyme-binding pockets, lectins, pharmacologic agent, synthetic peptides, antibody fragments, hydrophobic surface, hydrophyllic surface, any derivatives thereof or a combination thereof.

In another embodiment, the capture-particle comprises an analyte bound to the analyte binding portion, said analyte comprising: organic molecules, inorganic molecules, polypeptides, carbohydrates, nucleic acids, lipids, derivatives thereof or any combination thereof.

In other embodiments, the current invention is to a method for isolating analytes from a sample, comprising: contacting a sample comprising analytes with the capture-particles under conditions effective for said capture-particles to bind analytes of a defined molecular mass or particle size. In other embodiments the molecular sieve material is capable of expanding in volume, contracting in volume, changing its effective pore size or any combination thereof, in response to a physical or chemical treatment. The physical treatment can be applied energy and the method may further comprise applying energy to said capture-particles in an amount which is effective for expanding said molecular sieve material to allow said analytes to penetrate said material. The physical or chemical treatment may comprise thermal, electrical, magnetic, ultrasound, pressure, radiant, laser, osmotic, pH, or enzymatic treatment.

In other embodiments, the method of the current invention further comprises applying energy to said capture-particles in an amount which is effective for contracting, expanding or changing effective pore size of said capture-particle to trap said analytes therein.

In other embodiments of the current invention, the molecular sieve material is comprised of a polymeric network which is capable of contracting, expanding or changing its effective pore size in response to applied energy.

In other embodiments, the polymeric network comprises an N-alkyl substituted acrylamide. In other embodiments, the capture-particles further comprise an affinity ligand. The affinity ligand may comprise an antibody or protein, an aptamer, nucleic acid, a drug, a chemical, a metabolite, a lipid, a glycolipid, a phospholipid, a polypeptide, an affinity group, a metal group or any combination thereof.

In other embodiments, the capture-particles further comprise a detectable label. Additionally, the capture-particles may comprise an inner core and an outer shell, wherein said outer shell is comprised of a molecular sieve material. The inner core may comprise a second molecular sieve material and/or an affinity ligand.

In other embodiments, methods comprise the use of at least two different classes of capture-particles. Each class may comprise a different detectable label. In other embodiments of the current invention, the method uses capture-particles that are less than about 100 nm diameter in size.

In another embodiment, the current invention is to a method for isolating analytes from a sample, comprising: contacting a sample comprising analytes with solution-phase capture-particles under conditions effective for said capture-particles to selectively trap analytes of a defined molecular mass or particle size and a defined affinity, wherein said capture-particles comprise a molecular sieve material which is capable of excluding or permitting passage of an analyte of a defined particle size or molecular mass, and an affinity ligand capable of interacting with the analyte.

In other embodiments, the current invention is to a method for isolating analytes from a sample, comprising: contacting a sample comprising analytes with solution-phase capture-particles under conditions effective for said capture-particles to selectively trap analytes of a defined molecular mass or particle size.

In other embodiments, the current invention is to a method of diagnosing a disease comprising: a) contacting a sample comprising analytes with solution-phase capture-particles under conditions effective for said capture-particles to selectively bind analytes of a defined molecular mass, particle size, or defined affinity and b) identifying the analytes selectively bound to the capture particles, wherein the presence of analytes in the sample at identified concentrations is characteristic of a disease state. In other embodiments, the method further comprises detecting the presence of an analyte using a method selected from the group consisting of: enzyme-linked immunosorbent assay (ELISA), mass spectrometry, radioimmunoassay (RIA), microarray methods, immunoflourescence. northern blots, polymerase chain reaction (PCR), and in situ hybridization.

Another embodiment describes a method of preserving an analyte comprising: contacting a sample comprising said analyte with capture-particles under conditions effective for said capture-particles to selectively trap the analyte, said capture particles comprising a) a molecular sieve portion; and b) an analyte binding portion; wherein the molecular sieve portion, analyte binding portion or both comprise pore dimensions sufficient to exclude molecules larger than about 60 kDa.

In other embodiments, the current invention is a kit for the diagnosis, prognosis or monitoring of a disease state comprising: a container for collecting a fluid comprising analytes indicative of said disease state; and an amount of capture-particles for uptake and removal of said analytes, said capture-particles comprising: a) a molecular sieve portion; and b) an analyte binding portion; wherein the molecular sieve portion, analyte binding portion or both further comprise a crosslinked region having modified porosity.

In other embodiments, the kit for the diagnosis, prognosis or monitoring of a disease state comprising: a container for collecting a fluid comprising analytes indicative of said disease state; and an amount of capture-particles for uptake and removal of said analytes, said capture-particles comprising: a) a molecular sieve portion; and b) an analyte binding portion; wherein the molecular sieve portion, analyte binding portion or both comprise pore dimensions sufficient to exclude molecules larger than about 60 kDa.

BRIEF DESCRIPTION OF THE DRAWINGS

FIG. 2: Change in radius with temperature

FIG. 10: Example sequenced proteins or protein fragments fractionated by the particles.

FIG. 12: Reference proteins with isoelectric points and molecular weights.

DETAILED DESCRIPTION OF THE PREFERRED EMBODIMENTS

1. Nanoparticle Technology for Biomarker Enrichment and Preservation

Figure 1:
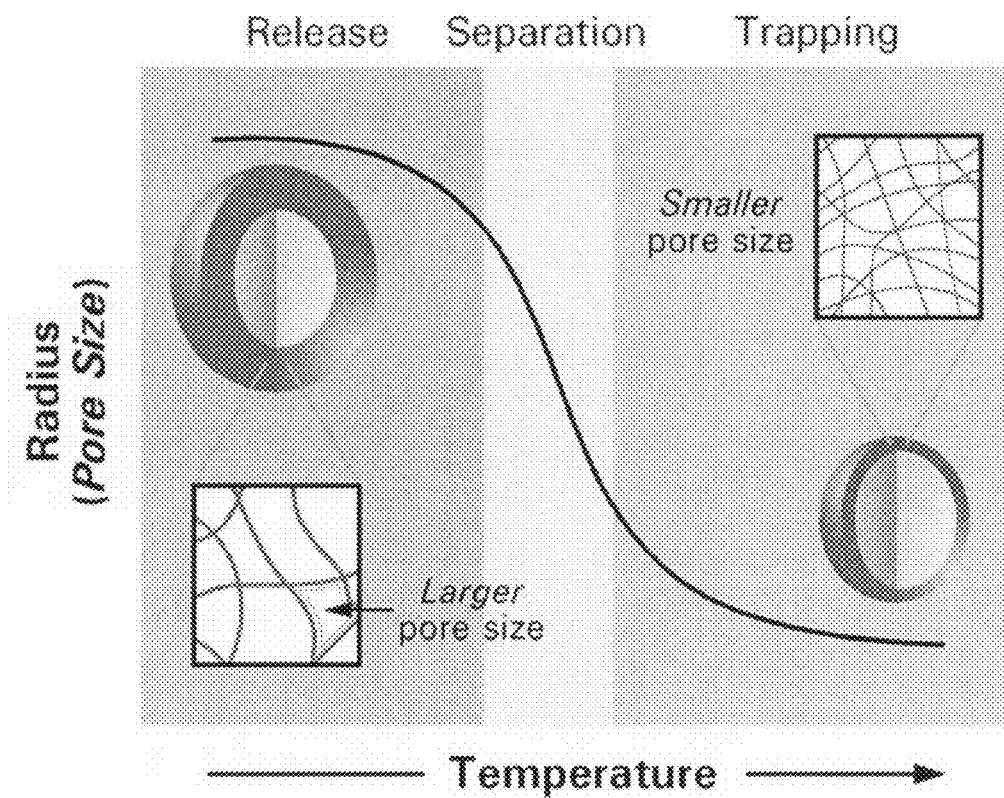
FIG. 1: Thermoresponsive particles change shape with changes in temperature.

In order to directly address the challenges of low abundance and preservation, this invention aims to create and evaluate "smart" nanoparticles that harvest (accumulate) selected classes of proteins in solution when added to complex mixtures of proteins such as plasma. The deliverable technology will be novel porous harvesting particles that have a unique structure capable of sorting molecules in solution based on both size and/or affinity. Moreover, the porosity of the particles may be thermally modifiable such that captured analyte (e.g. proteins) can later be released for analysis (FIG. 1). In addition, the proteins or chemical entities captured within the particles may be protected from degradation by enzymes or microbial growth.

This proposed technology can address the need for a means to enrich, isolate, and preserve low-abundance proteins and peptides in blood, urine and tissues. Such low-abundance molecules are expected to contain the most specific information about the state of a small disease lesion. In one embodiment the proposed technology consists of smart nanoparticles that can be pre-dispensed into a collection tube. Once the nanoparticles are suspended within the body fluid, or tissue lysate for example, the particles automatically (in one step) perform affinity chromatography and/or size exclusion chromatography in solution. The proteins and other metabolites (candidate biomarkers) captured within the smart particles can be therefore bonded and/or sequestered and protected from substantial degradation. By tuning the pore size and affinity properties of the smart particle populations, highly specific subsets of biomarkers can be captured and enriched from the entire volume of the procured fluid. This will enable room-temperature preservation and enrichment of low-molecular weight proteomic biomarkers. Following transport of the collection tube to the analysis lab, the nanoparticles can be easily isolated, so that the bound/sequestered biomarker cargo can be released for characterization using any analytical technique. In an alternative method, the biomarkers may be accessed via destructive treatment of the nanoparticles.

This technology can be of low cost and applicable in the routine clinical setting for seamless collection and immediate preservation of blood biomarkers. This transcends the large research hospital environment and extends most acutely to the private practice, where most patients receive therapy. The fabrication of large quantities of uniform "smart" one-micron-sized nanoparticles is certainly feasible, while other sizes larger or smaller are also possible and equally applicable. As described below, the particles can capture, accumulate, and purify labeled subsets of molecules from complex mixtures of molecules, such as serum.

2. Rationale for Choosing Smart Particles for Biomarker Harvesting

Thermoresponsive polymer gels are commonly referred to as 'smart gels' and display a controllable, nonlinear response to changes in local solution temperature, pH or external energy application (6, 7). Such polymers are comprised of crosslinked chains that undergo a thermodynamically favored phase separation leading to a change in gel volume (8, 9). The gels can be synthesized in bulk to take on the shape of the container or may be synthesized into particles ranging in diameter from 4 nm-100 μm (10, 11). In each case, the internal structure of the material is composed of flexible chains creating a soft, porous structure that can reversibly expand or contract according to the local conditions of the solution. An example of a "smart" polymer is poly(N-isopropylacrylamide) (pNIPAm), which has a lower critical solution temperature (LCST) of 31° C. in water (FIG. 2) (12). Below this temperature, the polymer matrix is swollen with solvent molecules, where hydrogen bonding occurs between the water and amide groups along the polymer backbone (12). As the temperature is increased above the LCST, hydrogen bonds are broken and water is excluded from the internal matrix, while hydrophobic interactions begin to dominate between the isopropyl groups, leading to a decrease in overall volume. This technology can be applied to separating biomarkers for identification.

One aspect of the present invention describes a molecular sieve portion of the capture-particles while another aspect pertains to an analyte binding (bait capture) portion. It is feasible to combine bait capture with molecular sieving into a single particle. A common means of fractionating complex mixtures of proteins is to use two classes of sequential chromatographic steps based on affinity and molecular sizing (14). Analysis of a complex and highly concentrated mixture such as plasma usually starts with dilution of the sample and removal of high-abundance proteins such as albumin prior to chromatography and gel electrophoresis. The smart particle technology disclosed herein accomplishes both steps of the separation without the use of chromatography or dilution. More specifically, added selectivity is enabled through the addition of bait molecules into the particle that bind/sequester a restricted population of biomarkers. Acrylic acid (AAc), for example, can be integrated into the particle and function as a tunable affinity resin. For example, at low pH (3.5), the AAc within the particle will be predominantly protonated, bearing a positive charge at that pH. At higher pH conditions, the AAc moieties will be either partially or predominantly deprotonated, which will create an intrinsic, charge based affinity element for positively charged proteins. By integrating AAc into the microgel, both the charge properties and the pore size of the particles provide a means to doubly fractionate proteins from complex mixtures like serum.

Another aspect of the invention deals with preservation by sequestration/binding of analytes therefore allowing one to stabilize analytes (e.g candidate biomarkers) in solution at room temperature. This can accomplished by their sequestration within the porous nanoparticles. It is hypothesized that proteins or molecules sequestered within the nanoparticles will not be available for access by solution phase degradative enzymes. Such enzymes may not be able to penetrate the pores of the particle because of their larger size.

Figure 3:
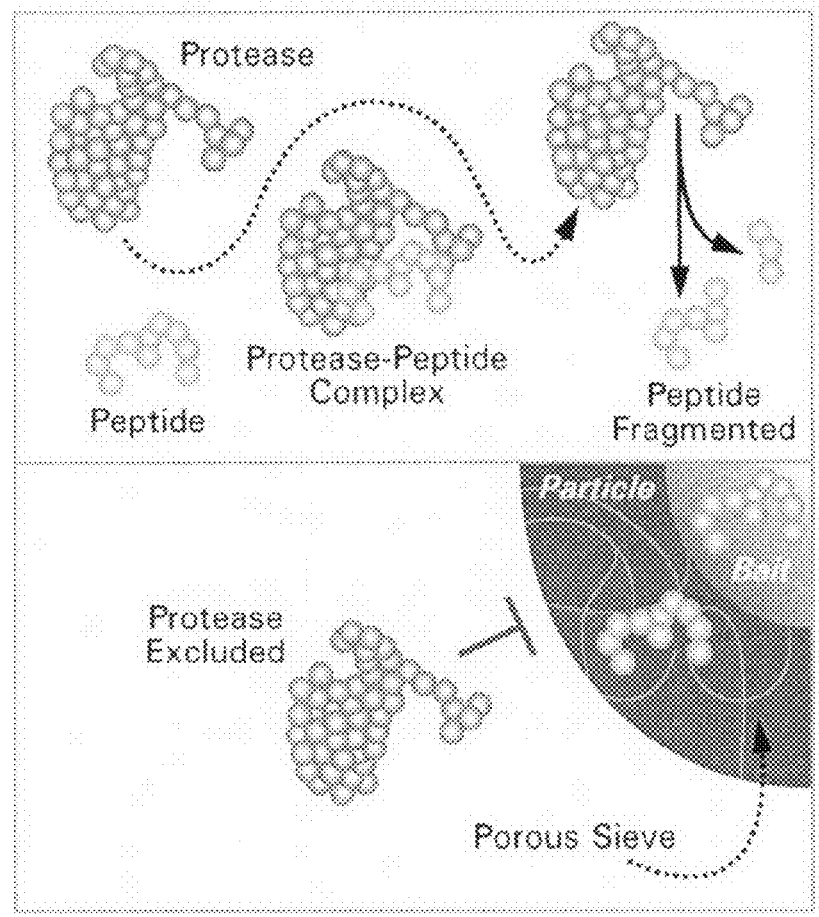
FIG. 3. Particles provide protection from proteolytic enzymes
Figure 4:
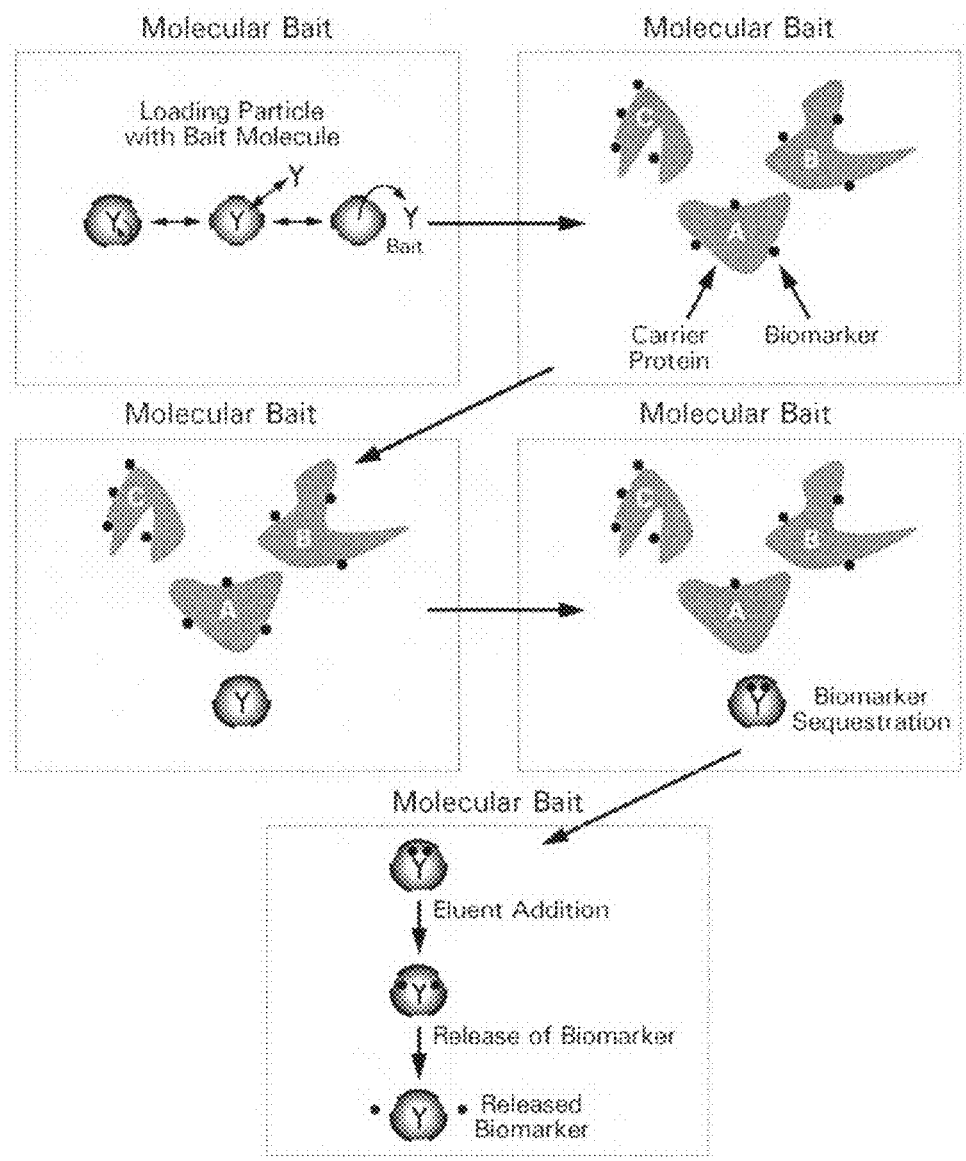
FIG. 4—Schematic view of one embodiment of the invention
Figure 5:
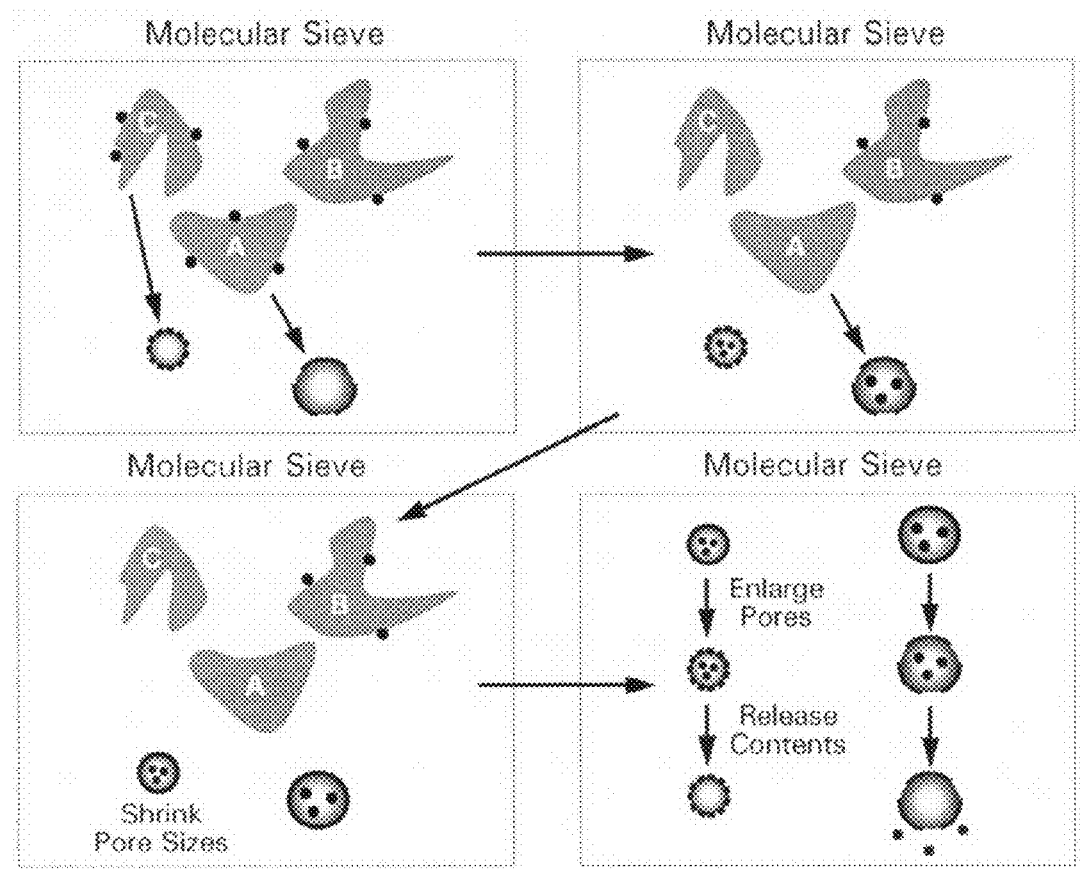
FIG. 5—Schematic view of one embodiment of the invention

Moreover, the affinity capture and immobilization of the candidate biomarker molecule will hinder the 3-D availability of the biomarker molecule such that the enzyme substrate complex can not functionally form within the particle (FIG. 3). This concept is somewhat analogous to the stabilization of proteins by precipitation or precipitation fixation. Applying capillary electrophoresis and mass spectrometry sequencing, we can study the degradation induced by exogenous serine or metalloproteinases, and compare the rate of fragmentation of proteins sequestered in particles versus those free in solution. Starting with defined mixtures of known and pre-characterized, or pre labeled proteins, we can progress to protein capture and stabilization within human serum and plasma reference samples.

3. Capture-Particles

The present invention provides a method and composition for separating and capturing molecular species from samples. In one embodiment of the invention, smart particles which have the ability to specifically capture molecular species having a defined molecular size, mass, and/or affinity characteristic are used to isolate molecules of interest from a sample typically containing a plurality of different molecular species with varying sizes. The particles can be added to the sample and then utilized to capture the molecular species of interest.

The particles can have one or more of the following functionalities: a) an ability to select the size, mass, and/or affinity property of the molecule to be captured, and/or b) an ability to capture and/or release the desired molecule in response to a physical or chemical treatment. The particles can accomplish this task in microvolumes, eliminating the need for the conventional multi-step procedures that utilize affinity columns, reverse phase columns, and other standard purification reagents and devices. Moreover, different classes of capture-particles can be used, each having different characteristics with respect to the molecule species they are able to capture, thus enabling a total extraction profile of multiple species to be performed in a single step.

One aspect of the inventions provides solution-phase capture-particles and methods of using them in isolating analytes from a sample, said method comprising one or more of the following steps including contacting a sample comprising analytes with solution-phase capture-particles under conditions effective for said capture-particles to selectively and optionally reversibly, trap analytes of a defined molecular mass or particle size, wherein said capture-particles comprise a molecular sieve material which is capable of trapping and optionally releasing an analyte of a defined particle size or molecular mass. Other aspects of the present invention, as described in more detail below, also employ specific capture-particles which non-reversibly trap analytes.

4. Sample

Any sample can be utilized without restriction, including biological fluids, such as blood, blood components, cerebral spinal fluid, lymph, cell lysates, tissue lysates, stool, urine, lymph, ascites, semen, ocular vitreous, etc.; environment samples, such as soil samples or extracts, ocean, pond, or river waters; water tower and drinking water samples; samples from chemical synthetic reactions; food samples; food processing samples (eg., from poultry processing plants), etc. For example, the methods can be used to detect contaminants in food, drinking water, and environment samples.

5. Analyte

The term "analyte" refers to any molecule of interest, including, organic molecules, inorganic molecules, polypeptides, carbohydrates, nucleic acids, lipids, derivatives thereof, and combinations thereof. Analytes include biomolecules which are shed from cell surfaces, released from cells (e.g., by exocytosis, lysis, etc.), metabolites, degradation products, protease digestion products, etc., without limitation. In one aspect of the invention, the methods can be utilized to entrap molecules in a biological fluid of a low molecular weight, especially those that would be excluded from the body by normal glomerular (kidney) filtration (e.g., molecules less that 30,000 Daltons) which are soluble and free-floating in the fluid or which are associated with carrier proteins. In general, the present invention can be used to capture any analyte of interest whose detection is desired including but not limited to sizes less than about 60,000 Da, less than about 50,000 Da, less than about 40,000 Da, less than about 30,000 Da, less than about 20,000 Da, less than about 10,000 Da, less than about 8,000 Da, less than about 6,000 Da, less than about 4,000 Da, less than about 2,000 Da, less than about 1,000 Da, including all individual values within each stated range.

With respect to body fluids, the capture-particles of the present invention can also be used to detect exogenous molecules, i.e., a molecule that was introduced into the body of the subject from whom the sample was obtained. Exogenous molecules can be actively or passively introduced into the subject. Examples of exogenous molecules include molecules present in, or in the form of, drugs, foods, tobacco, environmental products and contaminants (e.g., pesticides, carbon monoxide, etc), and essentially any molecule that enters the subject body through any route. Exogenous molecules also include their metabolites, by-products, and degradation products as processed or transformed in the body.

The capture particles can be utilized in any environment, including in vivo, ex vivo, and in vitro. For example, the particles can also be used as a tool to clear toxins from the blood in an in vivo or ex vivo context. For example, the particles can be utilized to remove toxic wastes from the blood, such as creatinine and urea, replacing the need for conventional dialysis.

6. Molecular Sieve Material

The capture-particles of the present invention can be comprised of a molecular sieve material (or molecular sieve portion). By this, it is meant that the material is porous, lattice-like, honeycombed, or has other properties that permit passage of analytes of a defined molecular mass or weight while excluding others. The size of the sieve pore is a determinant of whether the analyte can penetrate the capture-particle. The particle, itself, can be of any suitable size, e.g., less than about 10 μm, between about 10 μm and about 1 μm, between about 1 μm and about 100 nm, between about 1 nm and 100 nm, between about 5 nm and about 50 nm; between about 10 nm and about 20 nm; between about 10 nm and 1 nm; including all individual values within each recited range.

Pores in the sieve material can be designed based on the provided methods to diameters necessary for exclusion of unwanted molecules. Average pore sizes of between about 2 to about 20 nm, 1 nm to 1 μm, 1 nm to 10 nm, 1 nm to 50 nm, 10 nm to 50 nm, 50 nm to 100 nm, 10 nm to 200 nm, 50 nm to 500 nm, 1 nm to 10 nm, 1 nm to 5 nm, and other ranges are envisioned.

An optional feature of capture-particles is its ability to "trap" an analyte once it has entered the sieve material. The trapping may be achieved by using sieve materials which are capable of contracting and/or expanding in response to a physical or chemical treatment. For example, materials can be utilized which, when subjected to a chemical or physical treatment, contract or shrink, thereby trapping the analyte inside. Such materials can also be referred to as "smart materials" which have the ability to change shape or size by subject to a physical or chemical treatment. Any material having this property can be utilized without restriction, including, but not limited to, e.g., polyacrylamide and derivatives thereof; poly(N-isopropylacrylamide (e.g., Jones and Lyon, *Macromolecules*, 36:1988-1993, 2003; Jones and Lyon, *Macromolecules*, 33:8310-8306, 2000) and other N-alkyl substituted acrylamides; poly(N-vinylalkylamides); poly(methacrylic acid); poly(benzyl glutamate); poly(2-ethylacrylic acid); poly(4-vinylpyridine); ferroelectric liquid crystalline elastomers; piezoelectric polymers; "smart" gels, ceramics, alloys, and polymers, etc. See, also, e.g., Galaev et at., Pages 835-849; Zentel; Pages 850-860; Harrison and Ounaies, Pages 860-873; in *Encyclopedia of Smart Materials*, Volumes 1-2, Edited by, Schwartz, Mel© 2002 John Wiley & Sons. The capture-particles can be prepared routinely as known in the art or described in any of the above-mentioned references.

In one embodiment of the present invention the capture-particles do not contain any poly(N-isopropylacrylamide) constituent. Furthermore, capture particles in this embodiment also exclude poly(N-isopropylacrylamide-co-acrylic acid.)

a. Physical or Chemical Treatment of Sieve Material

Physical and/or chemical treatments that can be utilized to contract and/or expand the sieve material can comprise thermal, electrical, magnetic, ultrasound, pressure, radiant, laser, osmotic, pH, salt, enzymatic, oxidation/reduction, dehydration/rehydration, ultraviolet, radiation, high intensity red light, treatments.

The sieve material can reversibly or non-reversibly contract or shrink. For example, the capture-particles can be placed in a solution where the analytes are permitted to penetrate, and then non-reversibly shrunk to capture the analyte. This could be useful where the objective is to remove a contaminant from a solution, and it is not necessary to analyze or further evaluate the nature of the captured analyte, thus not requiring it to be expanded. Alternatively, non-reversible capture-particle can be broken apart by sonication or other disruptive forces which destroy the integrity of the particle.

In one embodiment the capture-particle is capable of expanding and contracting to allow for capture and/or sequestration of an analyte.

In another embodiment, the capture-particle does not expand or contract to any significant degree to enable increased or reduced uptake of an analyte. That is the volume of the particle is substantially fixed. Examples of such capture particles include particles comprising viral proteins, Clatherin, carbon nanotubes or species which do not permit the expansion/contraction described previously. An example illustrating preparation of a polygonal structure from Clatherin is described in Jaarsveld, et al., *Biochemistry* 1981, 20, 4129-4135 hereby incorporated by reference.

7. Analyte Binding (Affinity) Portion

The capture particles can comprise surface protein properties for selective analyte binding and/or can be modified by the attachment of moieties that confer such binding properties.

The capture-particles can further comprise an analyte binding, affinity ligand or "bait." Such terms can refer to substances which are capable of specifically attaching to an analyte of interest. Typical examples include, but are not limited to antibodies and derivatives thereof (e.g., Fab fragments and single-chain antibodies); binding proteins (e.g., receptors or fragments thereof for specific ligands); binding pairs (such as streptavidin/biotin); substrates; metals; chelating agents; nucleic acids; aptamers; enzyme-binding pockets; lectins; and/or an affinity group that is specific for an analyte of interest. The term "specific" has a functional meaning that the affinity ligand can be use to selectively bind to an analyte of interest in a sample and distinguish it from non-target analytes. It is specific in the sense that it can be used to detect analytes above background noise ("non-specific binding"). The affinity ligand can be selected such that it has a higher affinity for the analyte of interest than other components in the sample, allowing to out-compete any native binding proteins for the analyte.

The affinity ligands can be associated with the capture-particle in any suitable way. For example, they can used as a nucleus around which the sieve material is overlayed or deposited/nucleated in order to form the capture-particle; they can be directly incorporated into the sieve material prior to forming the particle (i.e., where the ligand is a component of the sieve material); they can be conventionally coupled (covalently or noncovalently) to the pore surfaces of the sieve material; etc. The affinity ligands can also be loaded into the capture particle by expanding the sieve material through appropriate physical or chemical treatment to reach a porosity that is large enough to admit the ligand, and then contacting the sieve material with the ligand under conditions effective for it to enter the particle. Once the particle is loaded with the affinity ligand, it can be shrunk by appropriate physical or chemical treatment, thereby reducing the sieve material's porosity, such that target analytes are still able to penetrate the particle, but larger analytes are excluded. The sieve porosity can be reduced after the affinity ligand loading step to pore size which is small enough to block the affinity ligand from diffusing out, making it unnecessary to link the affinity ligand to the sieve material. However, if desired, coupling processes can be used to link it to the sieve material.

Capture-particles baited with affinity ligands provide an analyte selection step, in addition to selection for analyte size or mass. For example, a capture-particle can be expanded to allow analytes to penetrate into it, and then the analytes can be further selected by their ability to specifically bind to an affinity ligand associated with the capture-particle. After the binding step is achieved (e.g., after equilibrium is reached), the particles can be separated and subjected to washing steps to remove unbound non-target analytes, and then optionally shrunk by a chemical or physical treatment.

The capture-particles can also further comprise antibodies as an affinity portion. Other candidate affinity portions include, but are not limited to, soluble receptors, polyamine analogs, antisense oligonucleotides, RNAi polynucleotides, ribozymes, and the like. Antibodies and soluble receptors are of particular interest as affinity portions where they target analytes of interest.

i. Antibodies

Affinity portions include antibodies and functional equivalents thereof that specifically bind to analytes. "Immunoglobulin" and "antibody" are used interchangeably and in their broadest sense herein. Thus, they encompass intact monoclonal antibodies, polyclonal antibodies, multispecific antibodies (e.g., bispecific antibodies) formed from at least two intact antibodies, and antibody fragments, so long as they exhibit the desired biological activity.

The variable domains of the heavy and light chain of an antibody recognize or bind to a particular epitope of a cognate antigen. The term "epitope" is used to refer to the specific binding sites or antigenic determinant on an antigen that the variable end of the immunoglobulin binds. Epitopes can be linear, i.e., be composed of a sequence of amino acid residues, conformational, such that an immunoglobulin recognizes a 3-D structure, or a combination thereof.

ii. Monoclonal and Polyclonal Antibodies

Immunoglobulins of the invention may be polyclonal or monoclonal, and may be produced by any of the well known methods in this art.

Polyclonal antibodies are preferably raised in animals by multiple subcutaneous (sc), intraperitoneal (ip) or intramuscular (im) injections of the relevant antigen and an adjuvant. It may be useful to conjugate the relevant antigen to a protein that is immunogenic in the species to be immunized, In addition, aggregating agents such as alum are suitably used to enhance the immune response.

The term "monoclonal antibody" refers to an antibody obtained from a population of substantially homogeneous antibodies. Monoclonal antibodies are highly specific, being directed against a single antigenic site. Furthermore, in contrast to polyclonal antibody preparations that typically include different antibodies directed against different determinants, each monoclonal antibody is directed against a single determinant on the antigen.

In addition to their specificity, monoclonal antibodies are advantageous in that they may be synthesized while uncontaminated by other immunoglobulins. For example, monoclonal antibodies may be produced by the hybridoma method or by recombinant DNA methods. Monoclonal antibodies also may be isolated from phage antibody libraries.

iii. Antibody Fragments

"Antibody fragments" comprise a portion of an intact antibody, preferably the antigen-binding or variable region thereof. Examples of antibody fragments include Fab, Fab', $F(ab')^2$, Fv fragments, diabodies, linear antibodies, single-chain antibody molecules, and multispecific antibodies formed from antibody fragments.

Various techniques have been developed for the production of antibody fragments. Traditionally, these fragments were derived via proteolytic digestion of intact antibodies. Two digestion methodologies that are well known in the art include papain digestion and pepsin treatment. Antibody fragments may now additionally be produced directly by recombinant host cells.

iv. Bispecific Antibodies

Bispecific antibodies of the invention are small antibody fragments with two antigen-binding sites. Each fragment comprises a heavy-chain variable domain connected to a light-chain variable domain in the same polypeptide chain. By using a linker that is too short to allow pairing between the two domains on the same chain, the domains are forced to pair with the complementary domains of another chain and create two antigen binding sites.

Methods for making bispecific antibodies are well known in the art. Traditional production of full length bispecific antibodies is based on the coexpression of two immunoglobulin heavy chain-light chain pairs, where the two chains have different specificities. Bispecific antibodies, however, may also be produced using leucine zippers.

The capture-particles can also further comprise detectable labels. By the term "detectable label," it is meant any moiety or substance that can be detected by any means. These include, quantum dots, fluorescent labels, enzymes, magnetic particles, etc. The detectable label can be associated with any region of the capture-particle, including its pores and exterior surface. Detectable labels are useful in a number of ways, including for sorting different classes of capture-particles. For example, different classes of capture-particles can be produced, where each class possesses a different characteristic (e.g., a different pore size and/or a different affinity-ligand), and each carries a different detectable label associated with each class of particles. This enables the property of the particle class (e.g., able to bind to a specific antigen) to be identified by determining which detectable label it bears, For instance, a particle with a single chain antibody for PSA can be labeled with FITC, and a particle containing an antibody for {alpha}-Methylacyl-CoA racemase (AMACR) can be labeled with TRITC. After performing the entrapment step, the particles can be sorted by flow cytometry using fluorescent-activated cell sorting, separating the HA-containing particles from the AMACR-containing particles.

8. Purification Methods

The capture particles of the current invention may be used in purification protocols to isolate analytes of interest from samples. As described above, the capture particles allow for purification of analytes based on size and affinity and this invention allows for quick isolation of analytes of interest from samples in order to preserve and study the analytes of interest. These analytes are preserved in the capture particles in order to prevent degradation from enzyme or other molecules in the sample.

9. Diagnostic Methods

The current invention also include a method of diagnosing a disease by contacting a sample comprising analytes with solution-phase capture-particles under conditions effective for the capture-particles to selectively bind analytes of a defined molecular mass, particle size, or defined affinity and then identifying the analytes selectively bound to the capture particles. The presence of analytes in the sample at identified concentrations would be characteristic of a disease state. Detecting the presence of an analyte could be done using methods well known to one of skill in the art such as enzyme-linked immunosorbent assay (ELISA), mass spectrometry, radioimmunoassay (RIA), microarray methods, immunoflourescence. northern blots, polymerase chain reaction (PCR), and in situ hybridization.

10. Kits

In certain kit embodiments, the capture particles are provided in a form suitable for use in purification or diagnostic methods. Kits generally provide the capture particles as well as reagents, instructions, and the necessary products for performing the purification or diagnostic method. These kits are envisioned for use by doctors in a medical setting to store samples or by others to begin purification and isolation of serum analytes.

The disclosure of all publications cited above are expressly incorporated herein by reference in their entireties to the same extent as if each were incorporated by reference individually.

In some embodiments the capture-particles comprise a molecular sieve portion and an analyte binding portion wherein the molecular sieve portion, analyte binding portion or both further comprise a cross-linked region having modified porosity.

In some embodiments, the capture particles comprise a molecular sieve portion and an analyte binding portion wherein the molecular sieve portion, analyte binding portion or both comprise pore dimensions sufficient to exclude molecules larger than about 60 kDa.

In one embodiment, said analyte binding portion comprises at least one type of moiety capable of chemically or electrostatically binding or sequestering a analyte. Accordingly, the analyte is effectively retained in a region within the capture-particle. Forces between the analyte and the analyte binding region may be that of, covalent bonding, van der waals forces, hydrophobic-hydrophobic, hydrogen bonding, hydrophyllic attraction, ionic attraction, or any combination thereof.

In another embodiment, the capture particles comprise pore sizes of between about 2 and about 20 nanometers with all individual values in between.

In another embodiment, the capture particles comprise pore sizes of less than about 100 nm including all individual values within this range.

In another embodiment, the capture particle comprises pore sizes dimensioned to exclude molecules having sizes greater than about 60 kDa.

In another embodiment, the capture particle comprises pore sizes dimensioned to exclude albumin.

In another embodiment, the capture particle comprises pore sized sufficiently large to permit passage of molecules of 1404 Da size while excluding albumin, molecules having sizes greater than about 60 kDa or both.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Smart Nanoporous Particle Synthesis and Characterization

The fabrication of "smart polymer" microgel particles and testing of their selective uptake of proteins and other small molecules is described below.

Particles were synthesized using N-Isopropylacrylamide (NIPAm), N,N'-methylenebisacrylamide (BIS) monomers (for experimental method, Example 8). Because the amount of crosslinker (Bis) added to the solution affects the functional porosity, two distinct concentrations of crosslinker (either 2% or 5%) were used to create the microgels. Large batches of 2% and 5% microgels were synthesized (greater than 20 grams each). In order to fabricate particles with a charge-based affinity bait within the gel matrix, microgel particles were created using NIPAm, BIS, and acrylic acid (AAc). The incorporation of acrylic acid within the particles provides pH-tunable affinity moieties. For example, at low pH (3.5), the AAc will be predominantly protonated, however, at higher pH conditions, the AAc moieties will be either partially or predominantly deprotonated, which will create an intrinsic, charge based affinity element contained within the particles.

Example 2

Microscopic Evaluation of Synthesized Particles

Figure 6:
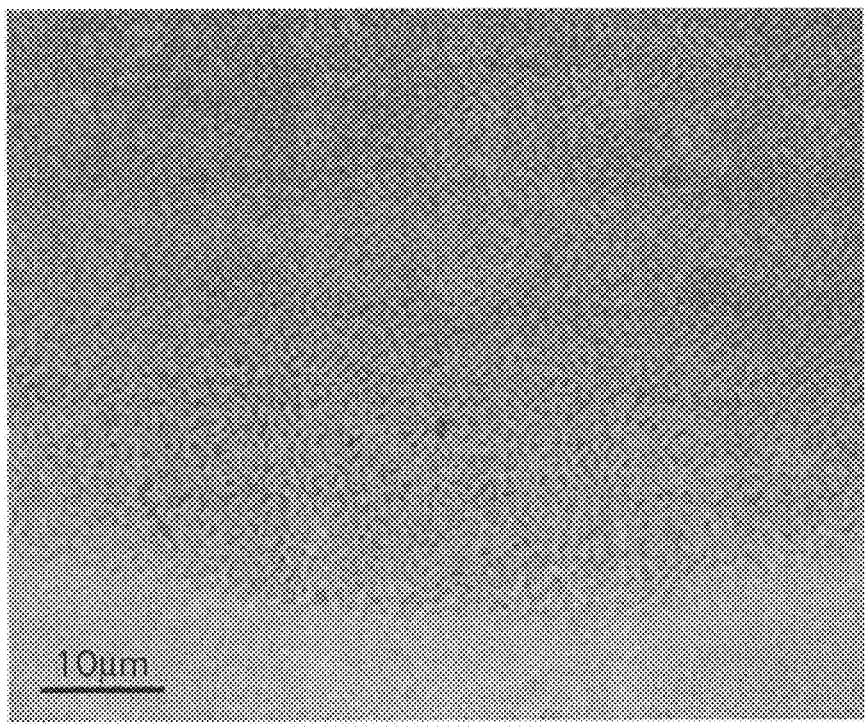
FIG. 6: Light microscopy image of microgel particles.
Figure 7:
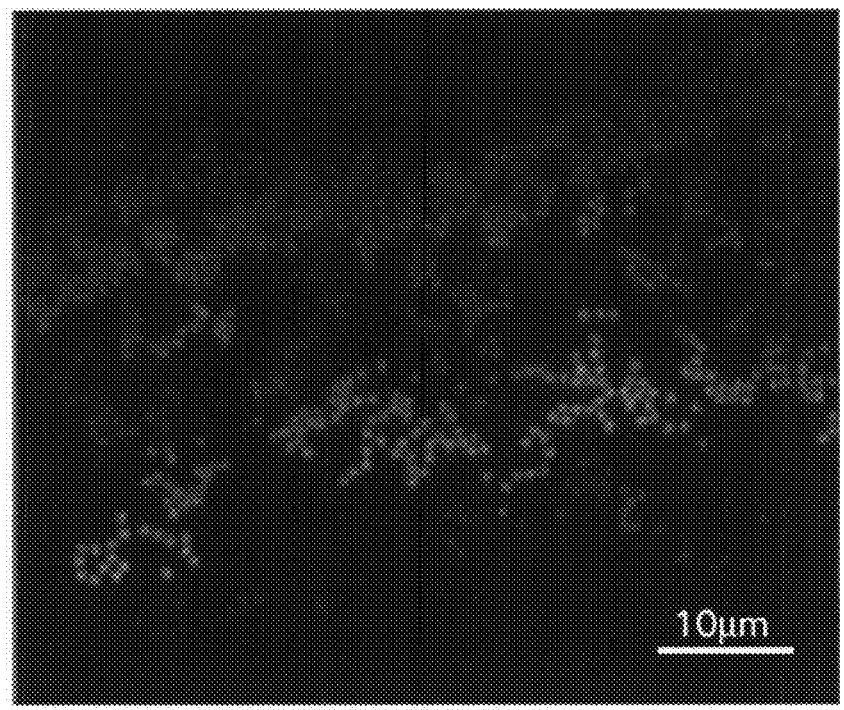
FIG. 7: Fluorescence microscopy image of microgel particles loaded with FITC.

Particles were examined using light microscopy and show a monodisperse uniform population (dia: 1 micron) (FIG. 6). Incubation of FITC with the particles and visualization using fluorescence microscopy showed internalization of the dye by the particles and a uniform population of particles (FIG. 7).

Example 3

Molecular Sequestration By Size

Figure 8:
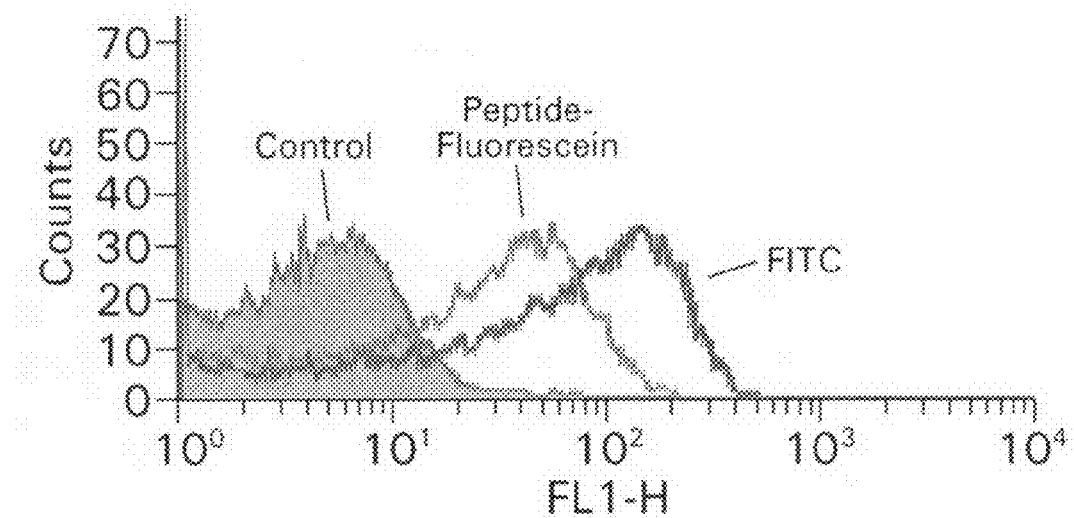
FIG. 8: Flow cytometry data showing uptake of FITC and labeled peptide by particles

In order to investigate the molecular exclusion properties of the particles, particles fabricated using 2% crosslinker concentration were incubated with three molecular species: FITC (MW 389), fluorescein linked to a small peptide (angiotensin II [MW 1404), and FITC linked to albumin (MW 66000). In-solution separation of three types of molecules was conducted. For each of the three fluorescent molecules (see below), 0.2 mL of purified microgels were placed into a 1.5 mL centrifuge tube. To this, 0.015 mL of either FITC, FITC-albumin, or Fluorescein-peptide (normalized to emitted fluorescent signal intensity) was added and mixed gently on a vortex. Each sample was diluted to 1.215 mL immediately prior to further investigations. Fluorescence uptake by the particles was measured using a FACScan (Becton Dickinson). A representative histogram of fluorescent dye uptake for the 2% particles is shown in FIG. 8. These experiments indicated that small FITC molecules readily migrated into the particles. The fluorescein-labeled peptide also migrated into the particle, but with a less intense signal shift when compared with FITC, indicating that the particles have a size-mediated selectivity. For both FITC- and fluorescein-labeled peptide, the level of internalization was higher in the 2% crosslinker population of particles than in the 5% crosslinker population (data not shown). This is consistent with a smaller nanopore size within the more highly crosslinked particle population, which would make internalization of the peptide more difficult. In both the 2% and 5% populations, albumin was excluded. The finding that albumin is excluded from the particles is an important initial step, as the goal of the smart particle program is to generate particles that sequester and accumulate candidate low-abundance biomarker molecules away from high-abundance resident proteins such as albumin.

Example 4

Sequestration of a Peptide from a Heterogeneous Protein Mixture

Figure 9:
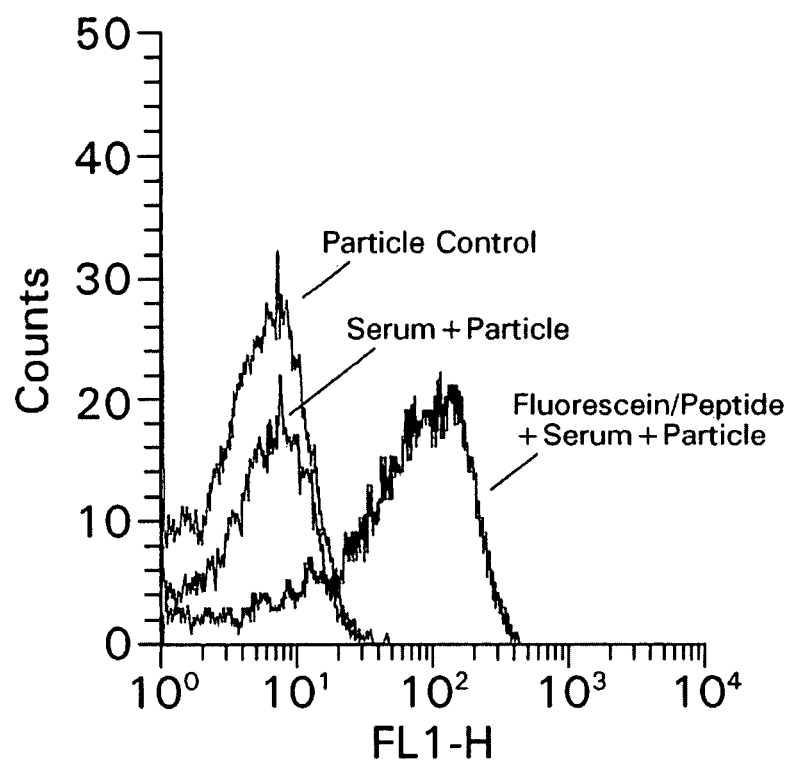
FIG. 9: Flow cytometry data showing uptake of FITC that had been spiked into serum.

In order to determine whether the particles could be used to isolate small molecules out of a heterogenous mixture, the particles made with 2% crosslinking agent were incubated with serum diluted 1:10 in water and spiked with the fluorescein-peptide described above. After the incubation, the particles were washed and peptide uptake detected using flow cytometry. The results are shown in FIG. 9. Notably, the particles showed a marked shift in fluorescence intensity when compared with plain particles or particles incubated with the heterogenous protein mixture without the spiked peptide. This experiment provides a demonstration of the sequestration properties of the particles.

Example 5

Serum Fractionation Using the Thermoresponsive Particles

2% crosslinker nano particle sieves were incubated with serum diluted 1:10 in water. The particles were incubated at 24° C. (the temperature at which the pores are maximally expanded) for 30 minutes. The particle/serum mixture was then placed into a 37° C. environment for 15 minutes in order to diminish the pore size of the particles and entrap molecules within the particles. The particles were then centrifuged for 15 minutes at 37° C. The supernatant (unentrapped proteins) was saved for SDS-PAGE analysis. The particles were washed twice with water for 15 minutes 37° C., followed by centrifugation at 37° C. In order to elute sequestered proteins, the particles were incubated for 15 minutes at 24° C., which opened the pores wider, followed by centrifugation at 24° C. The supernatant, or eluent, was collected and run on an SDS-PAGE gel. The gel demonstrated significant fractionation of the serum proteins by the particles. In order to identify the molecules fractionated through this technique, a gel slice was cut out of the gel and analyzed using electrospray ionization mass spectrometry. Tandem mass spectra were searched against human database (downloaded from the National Center for Biotechnology Information) with SEQUEST (16) using tryptic cleavage constraints. For a peptide to be considered legitimately identified, it had to achieve cross correlation scores of 1.5 for [M+H]1+, 2.0 for [M+2H]2+, 2.5 for [M+3H]3+, and a maximum probabilities of randomized identification of 0.001. A subset of molecules below 60,000 Da released from the 2% particles is listed in FIG. 10. These sequence identities demonstrate the feasibility of using these molecular harvesting particles for serum protein harvesting.

Example 6

This example shows the dose dependent uptake of FITC by 2% particles.

Volumes of 10 μl of 2% hydrogel particles were diluted in 90 μl of FITC aqueous solutions at different concentration (i.e. 0, 0.2, 1, 5, 20, 100, 500 μM). The samples were incubated overnight and then centrifuged at room temperature, at 16.1 rcf, and for 5 minutes. The pellet were then re-suspended in 100 ul of MilliQ water and centrifuged again with the same parameters. The pellet was re-suspended in 1 ml of water and fluorescence signal was analyzed by a flow cytometer to assess FITC uptake.

Figure 14:
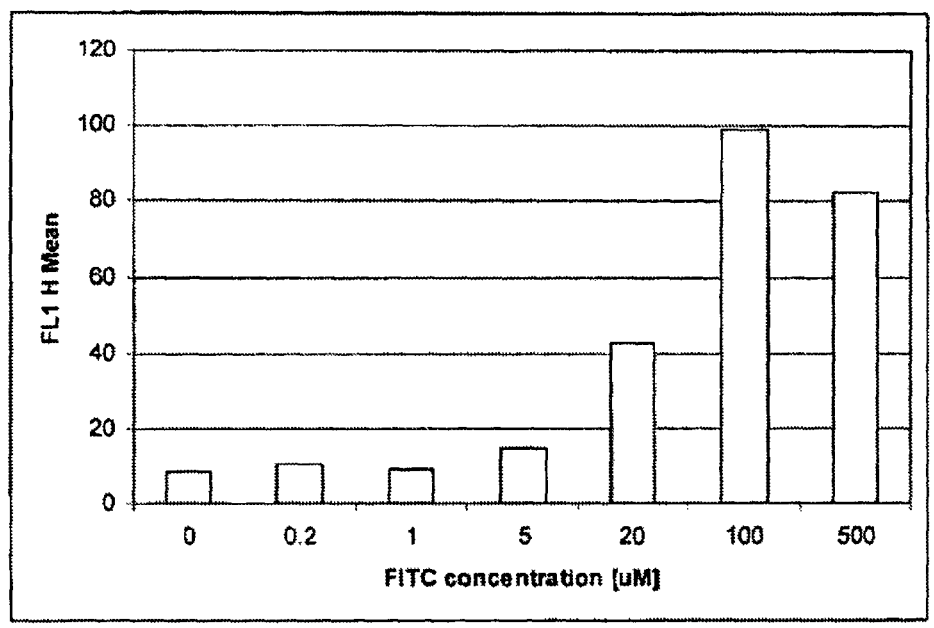
FIG. 14: A Graph displaying FITC concentration.

FIG. 14 displays a bar graph reporting means of fluorescent signal for each FITC concentration follows.

The above data demonstrate the dose dependent uptake of FITC by the particles.

Example 7

This example shows uptake of Insulin-Fluoroscein or FITC by 2% particles.

Volumes of 10 μl of 2% hydrogel particles were diluted in 90 μl of aqueous solutions with either FITC or insulin-fluoroscein. The samples were incubated overnight and then centrifuged at room temperature, at 16.1 rcf, and for 5 minutes. The pellet were then re-suspended in 100 ul of MilliQ water and centrifuged again with the same parameters. The pellet was re-suspended in 1 ml of water and fluorescence signal was analyzed by a flow cytometer to assess FITC uptake.

Figure 15:
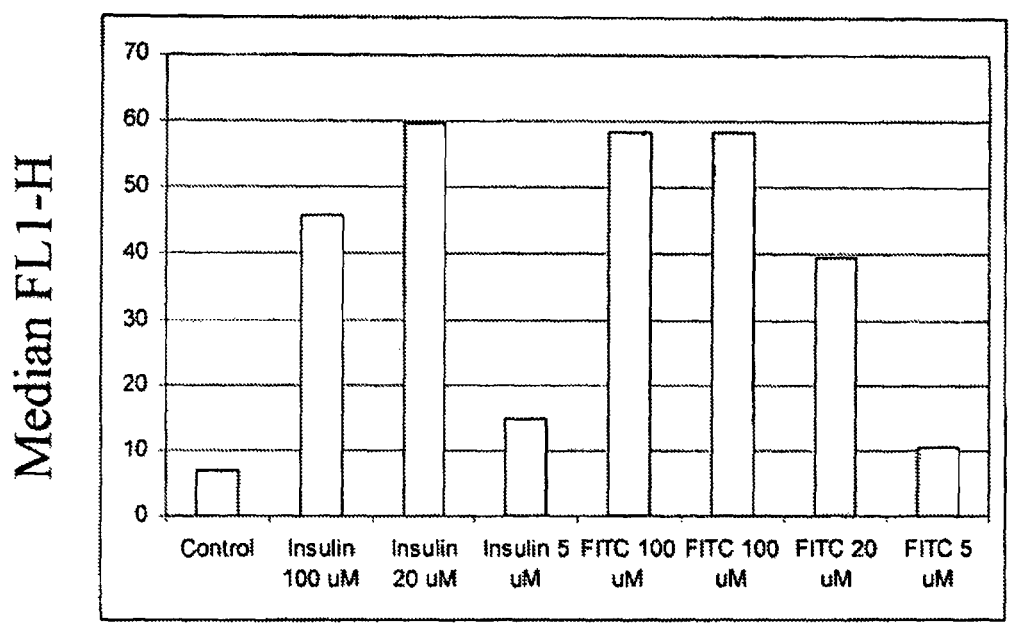
FIG. 15: Shows a bar graph reporting the median of fluorescent signal for each sample.

The bar graph shown in FIG. 15 is reporting median of fluorescent signal for each sample.

Control: particles with no additional fluorescent molecules.

The above data demonstrate the dose dependent uptake of insulin (about 6 kDa) and FITC (less than 1 kDa).

Example 8

Fabrication of "Smart Polymer" Harvesting Particle Technology

Micron-sized microgels incorporating N-Isopropylacrylamide (NIPAm) and N,N'-methylenebisacrylamide (BIS) by surfactant-free precipitation polymerization can be prepared. BIS is used as the crosslinker. Further, a preparation of particles containing acrylic acid (AAc) can be fabricated in order to incorporate a charge-based affinity bait into the particles.

Chemicals.

N-Isopropylacrylamide (NIPAm), N,N'-methylenebisacrylamide (BIS), ammonium persulfate (APS), acrylic acid (AAc) can be purchased from Sigma. Water for reactions, washing and loading is purified with a Millipore Milli-Q water purification system to a resistance of 18 MΩ and passed through a 0.2 μm filter.

Synthesis and Characterization of Hydrogel Sieve Nanoparticles with a Series of Molecular Size Exclusion Classes: Less than 50 kDa, 20 kDa, and 5 kDa.

Figure 11:
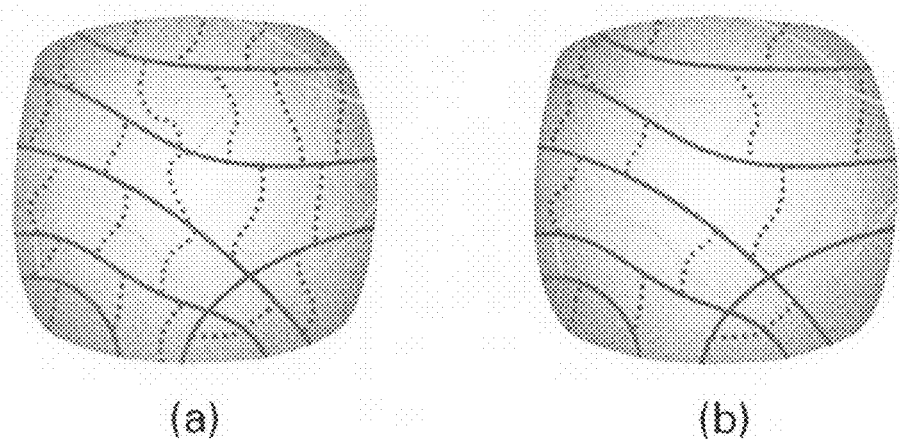
FIG. 11: Matrix with more (a) or less (b) crosslinking agent.

Microgels can be synthesized via precipitation polymerization in water as previously reported (12). The total monomer concentration (NIPAm and BIS) is 0.3 M. The BIS: NIPAm monomer ratio will determine the resultant network density and thus the average pore size. Particles can be made using varying amounts of crosslinker during polymerization, including 2% and 5% total concentration of crosslinking agent in order to vary the pore sizes of the particles See FIG. 11. The monomers are fully dissolved in 100 mL of water inside of a round bottom 150 mL 3-neck flask fitted with a condenser and thermometer at a medium stir rate (magnetic stirrer). The solution is heated to 70° C. over the period of 1 hour under a stream of nitrogen. A stable maximum stir rate is achieved and polymerization initiated with a 1.0 mL solution of 6 mM APS. The reaction is allowed to proceed for 3 hours under nitrogen. After cooling to room temperature overnight, 0.5 mL aliquots of the microgel solution are placed into individual 1.5 mL capacity centrifuge tubes and diluted with 1.0 mL of water. The samples are then centrifuged for 20 minutes at 23° C. and 16,100 rcf with an Eppendorf 5415R centrifuge. The supernatant is decanted and the microgels redispersed in water, again to a volume of 1.5 mL. This process is repeated for a total of five concentration/redispersion steps. Uniformity and size range is assessed using light microscopy as well as uptake of fluorescent dyes with fluorescence microscopy visualization. Flow cytometry also enables relative size to be assigned through the use of commercially available fluorescently labeled sizing particles as standards.

Synthesis and Characterization of Nanoparticle Sieves Containing an Affinity Bait.

Poly(NIPAm-co-AAc) microgel particles can be fabricated that have pH-tunable affinity moieties within the particle matrix. As an example reaction, NIPAm (1.3 g), BIS (0.10 g), and AAc (0.072 g) can be dissolved in 150 mL of H2O. APS is used as the initiator, as described above. With the integration of AAc into the particles, charged chemical elements are part of structure of the particles. For example, at low pH (3.5), the AAc is predominantly protonated, however, at higher pH conditions, the AAc moieties is either partially or predominantly deprotonated, which will create an intrinsic, charge based affinity element contained within the particles.

Example 9

Differential purification and isolation of proteins from defined molecular mixtures using the harvesting particle technology.

The capability of the particles to automatically (in one step) conduct size exclusion chromatography and/or affinity chromatography in solution is attainable. By tuning the pore size and affinity properties of the particle populations, highly specific subsets of proteins will be captured and enriched from protein mixtures. The proteomic tool kit for these studies includes capillary electrophoresis, flow cytometry, size chromatography separation of low molecular weight proteins by PrepCell gel elution, gel electrophoresis, and nanoflow reversed-phase liquid chromatography-tandem MS (nanoRPLC-MS/MS)

Demonstration of size-based molecular uptake by particles.

Assembly of Protein Study Set. An important initial step is to assemble a panel of protein reagents with distinct physicochemical properties and to use them to test the selectivity of particle preparations for protein subsets. FIG. 12 shows such an example panel, with proteins selected from 6000 Da to 45,000 Da (as well as albumin). These proteins have a range of isoelectric points, which provides a range of charge states at a given pH. This reference set can be supplemented with defined synthetic and natural peptides such as angiotensin and Pro-B-Type Natriuretic Peptide.

Labeling of Study Set Proteins:

Proteins from the study set can be labeled with fluorescent dyes, such as fluorescein and rhodamine. They can be purchased from commercially available sources or can be conjugated within the laboratory using standard conjugation techniques. The degree of fluorescent modification of the proteins can be measured and normalized. As described above, fluorescently labeled angiotensin peptide and albumin have been created and applied to feasibility studies using flow cytometry.

Protein Uptake/Exclusion Studies:

Fluorescently labeled molecules of distinct sizes can be incubated with microgel harvesting particles in order to understand the protein uptake properties of two distinct particle populations: 2% crosslinker particles (larger pore size) and 5% crosslinker particles (smaller pore size). The particles are in a detectable size range, for flow cytometry systems. This provides a system in which proteins labeled with dyes such as rhodamine or fluorescein can be detected in association with the particles. One can demonstrate the exclusion of fluorescently labeled albumin from the particles while showing uptake of fluorescently labeled molecules smaller than albumin. The crosslinking concentration can be titrated to achieve size exclusion in the following categories a) <50 kDa, b) <20 kDa and c) <5 kDa using the reference set. Briefly, molar equivalents of fluorescently labeled proteins can be incubated with the microgel particles for defined time periods (minutes to days), temperatures (24-37 C), and buffer conditions (aqueous [acidic, basic, physiologic pH] and organic solvents). The temperature and pH dependence of the particle pore sizes make them dynamic structures that require carefully controlled environmental conditions. The laden particles can then be separated from the supernatant by temperature-controlled centrifugation (Eppendorf temperature controlled microfuge, 16,100 rcf). The particles can then be washed in water followed by another round of temperature-controlled centrifugation. Uptake of the target proteins by the particles is then demonstrated by flow cytometry, using a Becton Dickinson FACScan cytometer. Retention profiles are measured based on the sizes and surface properties of the proteins as well as the temperatures and buffer conditions at which loading optimally occurs. An optimal "uptake" temperature can be identified at which target proteins are most efficiently sequestered by the particles.

Demonstration of affinity-based molecular uptake by particles.

An additional discriminatory feature, namely acrylic acid (AAc) charged affinity moieties, can be integrated into the particles within the three target size exclusion classes. Using AAc, the charge state of the particle bait can be tuned based on the pH of the solution in which they are suspended. At a lower pH (3.5), the AAc moieties are predominantly protonated. On the other hand, at higher pH conditions, the AAc moieties are either partially or predominantly deprotonated, which will create an intrinsic, charge based affinity element contained within the particles that is tunable based on the solvent conditions.

Protein Uptake/Exclusion Studies:

Using the experimental plan (fluorescently labeled protein study set and flow cytometry) described above, fluorescently labeled molecules of distinct size classes can be incubated with microgel harvesting particles in order to evaluate the effect of particle concentration and exclusion size on protein uptake properties of the AAc particles: The uptake is compared with the protein uptake properties of the plain particles. The proteins are incubated with the microgel particles for defined time periods (minutes to days), temperatures (24-37 C), and buffer conditions with a range of pH, from 3.0 to 10. Retention profiles can measured based on the sizes and surface properties of the proteins as well as the temperatures and buffer conditions at which loading optimally occurs.

Evaluation of the Yield and Time Course of the Controlled Uptake and Release of Targeted Proteins and Polypeptides from Defined Molecular Mixtures.

A critical component of the harvesting particle technology is the controlled release of the target proteins for further study and measurement. Building on the selective uptake of proteins by the particles, the below example focuses on studying the release properties of the particles.

Uptake of Protein by Particles with Size and/or Affinity Properties:

Particles can be loaded with proteins from the protein study set using previously determined optimal temperature, pH, time, and particle concentrations for loading a given protein into the particles.

Protein Release from Particles:

Release of proteins loaded into particles may be achieved thorough temperature change (control of pore size), pH change (alteration in charge of AAc moieties), chemical lysis of particles, or physical lysis of particles (such as sonication). Optimal release conditions of loaded conditions are determined depending on the affinity and abundance of the target analyte. Release of proteins from a particle preparation are measured by pelleting the particles by centrifugation and measuring the supernatant for the concentration of the proteins in the solution using gel electrophoresis, mass spectrometry and capillary electrophoresis. It is important to note that particles with captured proteins can be chemically or physically lysed following separation from the plasma to achieve 100 percent theoretical yield.

Size Chromatography Separation of Proteins by PrepCell Gel Elution.

Figure 13:
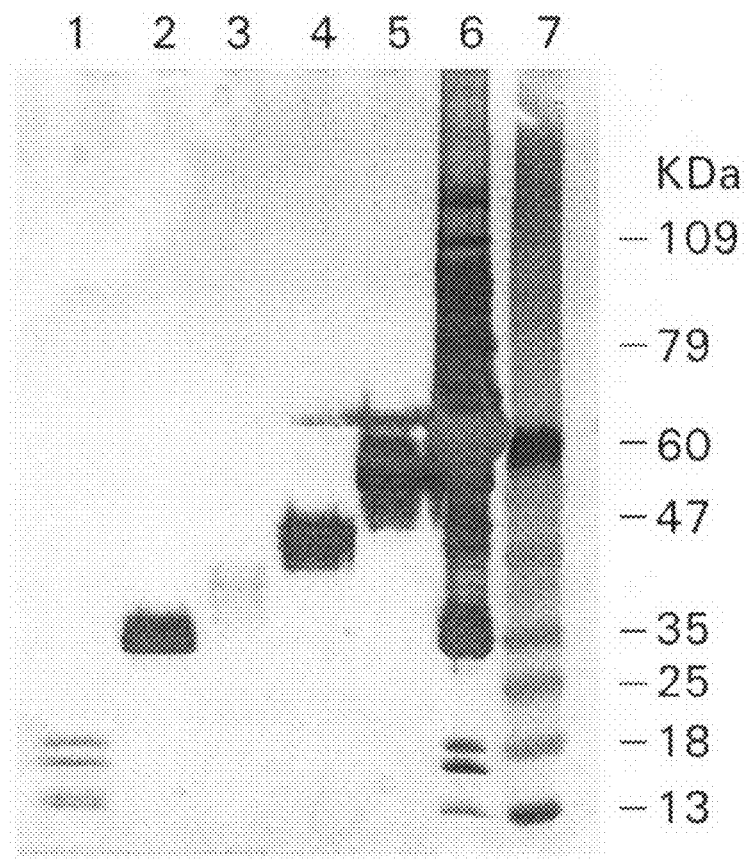
FIG. 13. Silver stained low molecular weight proteins fractionized by PrepCell. 100 [1.1 of serum was loaded to PrepCell. After 2 hours of electrophoresis, proteins migrated out of the gel and were subsequently collected from elution chamber at different time. Lane 1-5: 1/500 of the eluted proteins (equivalent to 0.18 [1.1 of raw serum), collected after 15, 45, 60, 90 and 120 minutes; lane 6: 0.18 [1.1 of raw serum; lane 7: protein marker.

Proteins eluted from particles can be fractionated using PrepCell technology. A large volume of a highly complex mixture, such as serum, can be separated into discrete size categories of proteins using this technique. As an example, 100 µl of serum was mixed with 1×SDS-PAGE loading buffer, boiled for 10 minutes, and loaded to PrepCell (Bio-Rad). 2 hours of electrophoresis was conducted, and eluted under continuous flow off the end of the gel. Low molecular weight proteins migrated out of the gel at earlier times and were eluted to collection tubes. Virtually 100% yield was achieved, with sharp size segmentation. See FIG. 13 for an example gel from such a procedure. This technology can be applied to proteins loaded and subsequently released from the smart particles. The eluted fractions can be digested in solution with trypsin and sequenced by mass spectrometry.

Nanoflow Reversed-Phase Liquid Chromatography-Tandem MS (nanoRPLC-MS/MS) and Bioinformatic Analysis Eluted proteins from PrepCell can be passed through detergent clean-up micro kit ProteoSpin (Norgen, Canada) to remove the SDS in the elution buffer that could interfere with mass spectrometry analysis. The cleaned proteins are reduced by 10 mM DTT, alkylated by 50 mM iodoacetamide, and digested by trypsin (from Promega) at 37° C. overnight. Tryptic peptides are further purified by Sep-Pak cartridges (Waters) and analyzed by reversed-phase liquid chromatography nanospray tandem mass spectrometry using a linear ion-trap mass spectrometer (LTQ, ThermoElectron)). Separation columns are slurry-packed with 5 µm, 200 Å pore size $C_{18}$ resin (Michrom BioResources) in 100 µm i.d.×10 cm long fused silica capillary (Polymicro Technologies)) with a laser-pulled tip. After sample injection, the column is washed for 5 minutes with mobile phase A (0.4% acetic acid) and peptides eluted using a linear gradient of 0% mobile phase B (0.4% acetic acid, 80% acetonitrile) to 50% mobile phase B in 30 minutes at 250 nanoliter/min, then to 100% B in an additional 5 minutes. The LTQ mass spectrometer is operated in a data-dependent mode in which each full MS scan is followed by five MS/MS scans where the five most abundant molecular ions are dynamically selected for collision-induced dissociation (CID) using a normalized collision energy of 35%. Tandem mass spectra are searched against human database (downloaded from the National Center for Biotechnology Information) with SEQUEST using tryptic cleavage constraints. For a peptide to be considered legitimately identified, it has to achieve cross correlation scores of 1.5 for [M+H]1+, 2.0 for [M+2H]2+, 2.5 for [M+3H]3+, and a maximum probabilities of randomized identification of 0.001. The generated protein lists is used to document release of proteins from the particles (16).

Capillary Electrophoresis:

Capillary Electrophoresis (CE) enables rapid fractionation of complex samples. In CE, a capillary is filled with a conductive fluid that is a buffer at a certain pH value. A sample is introduced from one end of the capillary using pressure and a high voltage is generated with separation based on size and charge. The migrating molecules pass through a light source that enables a spectrum of the molecules present to be generated. Using CE-based detection, particles are loaded with proteins previously shown to be taken up by the particular particle in defined environmental conditions (temperature, etc.). Following loading, the particles will be washed in water followed by centrifugation (16,100 rcf for 15 minutes). The particles will be resuspended and protein eluted using temperature, pH, and chemical and/or physical disruption. CE are performed to detect the released protein. Prior to running this assay, the spectral profile of the target proteins will be measured on the CE.

Stabilization and Preservation Using Standards and Human Serum/Plasma.

Using mass spectrometry-based detection, CE, and flow cytometry can demonstrate the sequestration, preservation, and controlled release of target protein analytes that have been added, or spiked, into heterogenous mixtures such as reference serum.

Microgel Particles can Protect Target Analytes from Enzymatic Degradation After They are Spiked into Reference Serum.

Flow Cytometry Studies to Document Particle Loading.

Classes of microgel particles (varying crosslinker concentration or AAc affinity bait) can incubated with serum that has been spiked with a fluorescent labeled protein of defined molecular weight. Optimal loading conditions can be defined (i.e. temperature, pH, time) as described above. After the incubation, the particles are centrifuged and washed once followed by centrifugation. Peptide uptake is detected using flow cytometry as described above. As described above, we have demonstrated that FITC labeled peptides spiked into serum can be sequestered with high efficiency into particles. These findings can be extended to include other molecules that will be spiked into serum at known concentrations, such as fluorescently labeled PSA (commercially available) and pro-brain natriuretic peptide (PBNP). PSA can be spiked into female serum (ranging from 0.5 to 25 ng/ml, which represents a clinically relevant range of PSA spanning healthy to cancer-bearing patients). PBNP can be spiked into serum at a concentration of 0.5 to 5 ng/ml. Both of these molecules have clinical significance for patients with prostate disease and heart disease, respectively. Because of clinical interest in these molecules, a number of studies have been performed on the stability of these molecules under routine handling conditions (24,25). Uptake of these spiked molecules can be documented using the flow cytometry assay as described above.

Studies to Document Protein Release (Elution) from Particles.

Once it is demonstrated that particles can be loaded with PSA or PBNP that has been spiked into serum, further studies can be performed to demonstrate that the targeted analytes may be released from the particles. Optimal elution conditions will be defined (i.e. temperature, pH, time, physical and/or chemical disruption of particles) as described above. As described above, PrepCell technology can be used to isolate fractions of eluted proteins within the expected size ranges. These are then analyzed using nanoflow reversed-phase liquid chromatography-tandem MS (nanoRPLC-MS/MS) coupled with bioinformatics analysis. The presence of the target analytes in the eluates from the particles, PSA or PBNP, will therefore be detected with high sensitivity. Quantitation of PSA or PBNP analytes can be achieved through measuring protein eluates using commercially available ELISA formats. Not only will the ELISA format allow quantification of eluted biomarker from the particles, but analyte amplification studies can be performed as well. NIST reference sera spiked with PSA can be incubated with a class of microgel particles. Using previously defined environmental conditions suitable for loading, the particles can be harvested by centrifugation, and the remaining serum solution removed. An additional aliquot of the serum reference can be added to the particles. Once again, the particles can be incubated with serum and then isolated by centrifugation. This cycle can be continued "n" times to study the loading plateau. The particles are then be treated with eluent, or release, conditions (time, temperature, physical or chemical disruption), and the amount of PSA present in the eluent is compared with one round of serum exposure using ELISA. This type of analyte amplification mimics the role that carrier proteins play in the serum, by providing a site for sequestration and accumulation for small, low abundance analytes. Through this strategy of amplification, the technology meets a critical need stated above, namely, the amplification and isolation of low abundance disease markers from serum.

Demonstration of Size-Based and/or Affinity-Based Loading/Release of Known Serum Proteins, Polypeptides, and Other Small Molecules by the Microgel Particles.

An important critical need is the development of preservative modalities that protect important biomarkers from degradation by proteinases. If molecular biomarkers can be sequestered within matrices, such as that found in the microgel particles, then they could be protected from enzymatic degradation processes. To test this novel hypothesis, PSA can be incubated with trypsin with and without the presence of microgel particles using loading conditions previously determined to optimal for the PSA/particle pairing. The presence of cleavage fragments can be detected by either capillary electrophoresis or nanoRPLC-MS/MS. The proteins incubated and internalized by the particles will avoid proteolytic degradation. NIST serum reference standards spiked with PSA can be incubated for a range of time periods without the presence of protective microgel particles. The relative of whole PSA versus PSA fragmented by endogenous or exogenously added proteinases can be evaluated using a Bland Altman Plot (24,25) for a range of concentrations and times. PBNP can be studied in the same way.

Demonstration that the Microgel Particles Sequester Known and Previously Unknown Low-Abundance Proteins and Peptides in Reference Serum.

Various classes of microgel particles, including particles containing AAc affinity bait, can be incubated with serum diluted 1:10 in water at varying temperatures, times, and a range physical conditions (pressure or sonication). Loaded proteins can be entrapped by changing the temperature to 37 C for varying time periods, which will markedly diminish the pore size. The particles can be washed multiple times at 37 C in order to remove unloaded proteins. In order to elute sequestered proteins, the particles can be incubated using a range of time, temperature, solvents and physical disruption techniques. Particles and particle fragments can be pelleted by centrifugation. The supernatant, or eluent, can be run on a PrepCell device in order to size fractionate the eluted proteins. The fractionated eluent can then be analyzed by nanoRPLC-MS/MS. Tandem mass spectra are searched against human database (downloaded from the National Center for Biotechnology Information) with SEQUEST (16) using tryptic cleavage constraints. For a peptide to be considered legitimately identified, it will achieve cross correlation scores of 1.5 for [M+H]1+, 2.0 for [M+2H]2+, 2.5 for [M+3H]3+, and a maximum probabilities of randomized identification of 0.001. Sets of sequence identities can be cataloged and linked to the loading and release conditions used for the particular microgel assay.

Example 10

This example shows uptake of FITC by 2% particles in a time course study

Volumes of 10 μl of 2% hydrogel particles were diluted in 90 μl of FITC aqueous solutions at 20 μM. The samples were incubated overnight and then centrifuged at room temperature, at 16.1 rcf, and for 5 minutes. The pellet were then re-suspended in 100 ul of MilliQ water and centrifuged again with the same parameters. The pellet was re-suspended in 1 ml of water and fluorescence signal was analyzed by a flow cytometer to assess FITC uptake.

Figure 16:
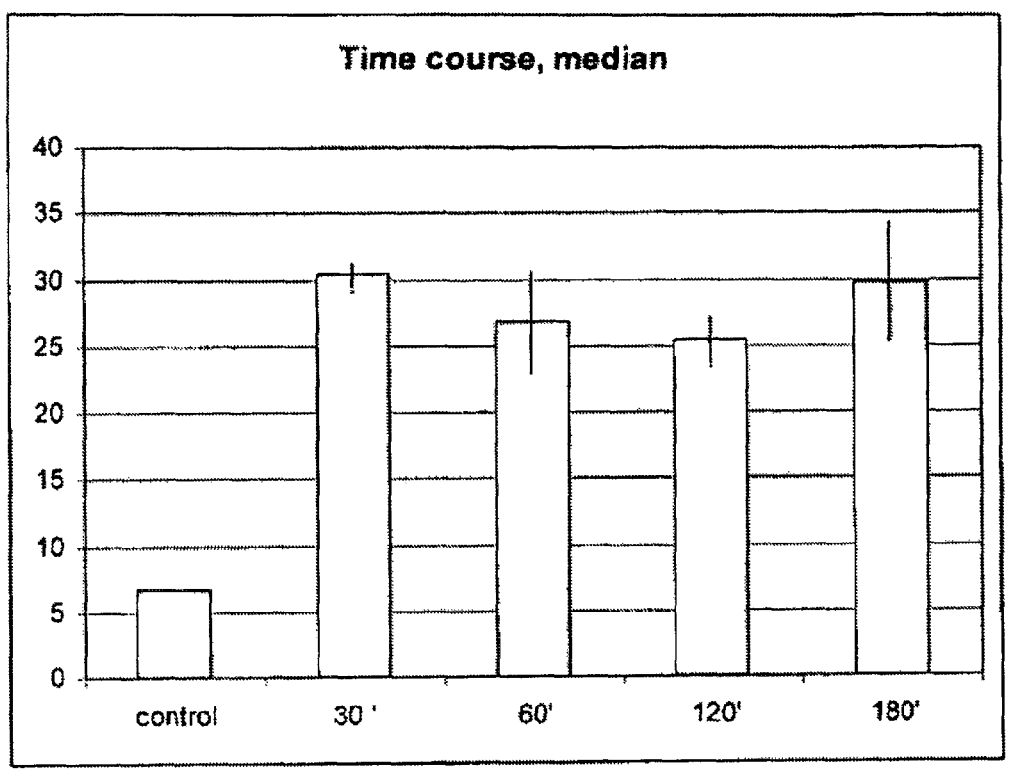
FIG. 16: Displays a bar graph displaying the median data.

A bar graph is shown reporting the median data in FIG. 16.

The above data demonstrate that between 30 and 180 minutes incubation of particles with FITC shows no significant change in detection of FITC uptake.

REFERENCES

1. Aebersold, R., L. Anderson, R. Caprioli, B. Druker, L. Hartwell, and R. Smith. 2005. Perspective: a program to improve protein biomarker discovery for cancer. *J Proteome Res* 4:1104.
2. Etzioni, R., N. Urban, S. Ramsey, M. McIntosh, S. Schwartz, B. Reid, J. Radich, G. Anderson, and L. Hartwell. 2003. The case for early detection. *Nat Rev Cancer* 3:243.
3. Anderson, N. L., and N. G. Anderson. 2002. The human plasma proteome: history, character, and diagnostic prospects. *Mol Cell Proteomics* 1:845.
4. Villanueva, J., D. R. Shaffer, J. Philip, C. A. Chaparro, H. Erdjument-Bromage, A. B. Olshen, M. Fleisher, H. Lilja, E. Brogi, J. Boyd, M. Sanchez-Carbayo, E. C. Holland, C. Cordon-Cardo, H. I. Scher, and P. Tempst. 2006. Differential exoprotease activities confer tumor-specific serum peptidome patterns. *J Clin Invest* 116:271.
5. Elias, J. E., W. Haas, B. K. Faherty, and S. P. Gygi. 2005. Comparative evaluation of mass spectrometry platforms used in large-scale proteomics investigations. *Nat Methods* 2:667.
6. Saunders, B. R., and B. Vincent. 1999. Microgel particles as model colloids: theory, properties and applications. *Advances in Colloid and Interface Science* 80:1.
7. Pelton, R. 2000. Temperature-sensitive aqueous microgels. *Advances in Colloid and Interface Science* 85:1.
8. Tanaka, T., G. Swislow, and I. Ohmine. 1979. Phase Separation and Gelation in Gelatin Gels. *Phys. Rev. Lett.* 42:1556.
9. Tanaka, T. 1978. Collapse of Gels and the Critical Endpoint. *Phys. Rev. Lett.* 40:820.
10. Tanaka, T., D. J. Fillmore, S.-T. Sun, I. Nishio, G. Swislow, and A. Shah. 1980. Phase Transitions in Ionic Gels. *Phys. Rev. Lett.* 45:1636.
11. Tanaka, T., E. Sato, Y. Hirokawa, S. Hirotsu, and J. Peetermans. 1985. Critical Kinetics of Volume Phase Transition of Gels. *Phys. Rev. Lett.* 55:2455.
12. Jones, C. D. 2003. Poly(N-Isopropylacrylamide) Based Microgels: I. Fundamental Properties of Core/Shell Microgels. II. Assembly and Photothermal Patterning of Microgel Colloidal Crystals. In *School of Chemistry and Biochemistry*. Georgia Institute of Technology, Atlanta, Ga., p. 193.
13. Sassi, A. P., A. J. Shaw, S. M. Han, H. W. Blanch, and J. M. Prausnitz. 1996. Partitioning of proteins and small biomolecules in temperature- and pH-sensitive hydrogels. *Polymer* 37:2151.
14. Adkins, J. N., S. M. Varnum, K. J. Auberry, R. J. Moore, N. H. Angell, R. D. Smith, D. L. Springer, and J. G. Pounds. 2002. Toward a human blood serum proteome: analysis by multidimensional separation coupled with mass spectrometry. *Mol Cell Proteomics* 1:947.
15. Lowenthal, M. S., A. I. Mehta, K. Frogale, R. W. Bandle, R. P. Araujo, B. L. Hood, T. D. Veenstra, T. P. Conrads, P. Goldsmith, D. Fishman, E. F. Petricoin, 3rd, and L. A. Liotta. 2005. Analysis of albumin-associated peptides and proteins from ovarian cancer patients. *Clin Chem* 51:1933.
16. Yates, J. R., 3rd, J. K. Eng, A. L. McCormack, and D. Schieltz. 1995. Method to correlate tandem mass spectra of modified peptides to amino acid sequences in the protein database. *Anal Chem* 67:1426.
17. Jones, C. D., and L. A. Lyon. 2000. Synthesis and Characterization of Multiresponsive Core-Shell Microgels. *Macromolecules* 33:8301.
18. Nayak, S., and L. A. Lyon. 2005. Soft nanotechnology with soft nanoparticles. *Angew Chem Int Ed Engl* 44:7686.
19. Nayak, S., and L. A. Lyon. 2004. Ligand-functionalized core/shell microgels with permselective shells. *Angewandte Chemie-International Edition* 43:6706.
20. Nolan, C. M., C. D. Reyes, J. D. Debord, A. J. Garcia, and L. A. Lyon. 2005. Phase transition behavior, protein adsorption, and cell adhesion resistance of poly(ethylene glycol) cross-linked microgel particles. *Biomacromolecules* 6:2032.
21. Gan, D. J., and L. A. Lyon. 2003. Fluorescence nonradiative energy transfer analysis of crosslinker heterogeneity in core-shell hydrogel nanoparticles. *Analytica Chimica Acta* 496:53.
22. Murray, J. D. 2003. *Mathematical Biology*. Springer-Verlag, Berlin.
23. Bowen, R. M. 1976. *Theory of Mixtures*. Academic Press, New York.
24. Gan, D. J., and L. A. Lyon. 2002. Synthesis and protein adsorption resistance of PEG-modified poly(N-isopropylacrylamide) core/shell microgels. *Macromolecules* 35:9634.
25. Liu, T.-Y., S.-H. Hu, K.-H. Liu, D.-M. Liu, and S.-Y. Chen. Preparation and characterization of smart magnetic hydrogels and its use for drug release. *Journal of Magnetism and Magnetic Materials In Press, Corrected Proof.*
26. Downie, P. F., S. Talwar, I. B. Squire, J. E. Davies, D. B. Barnett, and L. L. Ng. 1999. Assessment of the stability of N-terminal pro-brain natriuretic peptide in vitro: implications for assessment of left ventricular dysfunction. *Clin Sci (Lond)* 97:255.
27. Ulmert, D., C. Becker, J. A. Nilsson, T. Piironen, T. Bjork, J. Hugosson, G. Berglund, and H. Lilja. 2006. Reproducibility and accuracy of measurements of free and total prostate-specific antigen in serum vs plasma after long-term storage at −20 degrees C. *Clin Chem* 52:235.

What is claimed is:

1. A capture-particle consisting of:
   a) an outer molecular sieve portion; and
   b) an inner analyte binding portion with reactive organic affinity molecules configured for binding and sequestering analytes such that there are no dyes used for signaling detection;
   wherein the molecular sieve portion, analyte binding portion or both further comprise a cross-linked region having porosity physically configured to permit passage of analytes of a defined molecular mass or weight such that there is no chemical cleaving.

2. The capture-particle of claim 1 wherein said analyte binding portion comprises at least one type of moiety capable of chemically or electrostatically binding or sequestering an analyte.

3. The capture-particle of claim 1 wherein the analyte binding portion comprises a carboxy group, amine group, lipid, phosphoprotein, phospholipids, amide group, hydroxyl group, ester group, acrylic group, thiol group, acrylic acid, antibodies, binding proteins, binding pairs, metals, chelating agents, nucleic acids, aptamers, enzyme-binding pockets, lectins, pharmacologic agent, synthetic peptides, antibody fragments, hydrophobic surface, hydrophyllic surface, any derivatives thereof or a combination thereof.

4. The capture-particle of claim 1 further comprising an analyte bound to the analyte binding portion, said analyte comprising: organic molecules, inorganic molecules, polypeptides, carbohydrates, nucleic acids, lipids, derivatives thereof or any combination thereof.

5. The capture-particle of claim 1 wherein the molecular sieve portion is an outer shell enclosing an inner core, said inner core comprising the analyte binding portion.

6. The capture-particle of claim 1 having an average particle size radius of less than about 100μ.

7. The capture-particle of claim 1 wherein the molecular sieve portion, analyte binding portion or both comprise: polyacrylamide, poly(Nisopropylacrylamide), N-alkyl substituted polyacrylamide, poly(N-vinylalkylamide), poly(methacrylic acid), poly(benzyl glutamate), ply(2-ethylacrylic acid), poly(4-vinylpyridine), derivatives thereof or any combination thereof.

8. The capture-particle of claim 1 wherein the cross-linked region comprises N,N'-methylenebisacrylamide, ethylene glycol dimethacrylate, tetraethylene glycol dimethacrylate, poly(ethyleneglycol)dimethacrylate or any combination thereof.

9. The capture-particle of claim 1 wherein the molecular sieve portion, analyte binder portion or both comprise a hydrogel.

10. The capture-particle of claim 1 wherein the molecular sieve portion, analyte binding portion or both have an average pore size of between about 2 to about 20 nm.

11. The capture-particle of claim 1 the molecular sieve portion, analyte binding portion or both have an average pore size of less than about 100 nm.

12. The capture-particle of claim 1 wherein said capture-particle releases a bonded or sequestered analyte, changes volume or both when exposed to a physical or chemical treatment.

13. The capture-particle of claim 12 wherein the physical or chemical treatment comprises exposure to: electrical charge, hydrostatic pressure, change in pH, change in temperature, acidic agent, basic agent, UV, ultrasound, x-ray, or a combination thereof.

14. The capture-particle of claim 1 having the ability to uptake a 1404 Da peptide with substantially no uptake of albumin.

15. The capture-particle of claim 1 having the ability to uptake insulin.

16. A kit for the diagnosis, prognosis or monitoring of a disease state consisting of:
   a container for collecting a fluid comprising analytes indicative of said disease state; and an amount of capture-particles for uptake and removal of said analytes, said capture-particles consisting of:
  a) an outer molecular sieve portion; and
  b) an inner analyte binding portion with reactive organic affinity molecules configured for binding and sequestering analytes such that there are no dyes used for signaling detection;
  wherein the molecular sieve portion, analyte binding portion or both further comprise a cross-linked region having porosity physically configured to permit passage of analytes of a defined molecular mass or weight such that there is no chemical cleaving.

* * * * *